US008563943B2

(12) United States Patent
Iwata et al.

(10) Patent No.: US 8,563,943 B2
(45) Date of Patent: Oct. 22, 2013

(54) PARTICLE BEAM IRRADIATION APPARATUS, PARTICLE BEAM THERAPY SYSTEM, AND DATA DISPLAY PROGRAM

(75) Inventors: Takaaki Iwata, Chiyoda-ku (JP); Toshiyuki Hokodate, Chiyoda-ku (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 149 days.

(21) Appl. No.: 13/255,027

(22) PCT Filed: Dec. 24, 2010

(86) PCT No.: PCT/JP2010/073373
§ 371 (c)(1), (2), (4) Date: Sep. 6, 2011

(87) PCT Pub. No.: WO2012/086062
PCT Pub. Date: Jun. 28, 2012

(65) Prior Publication Data
US 2012/0161030 A1 Jun. 28, 2012

(51) Int. Cl.
*A61N 5/10* (2006.01)

(52) U.S. Cl.
USPC .................. 250/397; 250/396 MR; 250/398; 250/492.21; 378/65

(58) Field of Classification Search
USPC ............. 250/397, 396 R, 396 ML, 398, 526, 250/492.1, 492.21, 492.22, 492.23, 492.3, 250/503.1, 505.1; 378/51, 64, 65, 901
See application file for complete search history.

(56) References Cited

U.S. PATENT DOCUMENTS

| | | | | |
|---|---|---|---|---|
| 6,298,115 | B1 * | 10/2001 | Nilsson | 378/65 |
| 7,856,082 | B2 * | 12/2010 | Flynn et al. | 378/65 |
| 7,947,969 | B2 * | 5/2011 | Pu | 250/505.1 |
| 8,238,516 | B2 * | 8/2012 | Sakurai et al. | 378/65 |
| 2007/0211856 | A1 * | 9/2007 | Urano et al. | 378/65 |

(Continued)

FOREIGN PATENT DOCUMENTS

| | | | |
|---|---|---|---|
| EP | 2 078 537 | A1 | 7/2009 |
| JP | 2009-039219 | A | 2/2009 |

(Continued)

OTHER PUBLICATIONS

International Search Report (PCT/ISA/210) issued on Jan. 25, 2011, by Japanese Patent Office as the International Searching Authority for International Application No. PCT/JP2010/073373.

*Primary Examiner* — Bernard E Souw
(74) *Attorney, Agent, or Firm* — Buchanan Ingersoll & Rooney PC

(57) ABSTRACT

A particle beam irradiation apparatus There is provided a data processing apparatus that displays on a display unit a measured irradiation position value and an irradiation position value error, which is the error of the measured irradiation position relevant value related to the irradiation position of charged particle beam with respect to a desired irradiation position value related to a desired irradiation position, so that the measured irradiation position relevant value and the irradiation position relevant value error correspond to each other. The data processing apparatus displays a desired value display figure indicating a desired irradiation position relevant value at the coordinates of the desired irradiation position value and a measured value display figure at display coordinates, which are coordinates obtained by adding the desired irradiation position value to the coordinates acquired by arithmetically operating an irradiation position value error with deformation coefficients, and displays a line that connects the measured value display figure with the desired value display figure.

20 Claims, 14 Drawing Sheets

(56) References Cited

U.S. PATENT DOCUMENTS

| | | | | |
|---|---|---|---|---|
| 2007/0211857 | A1* | 9/2007 | Urano et al. | 378/65 |
| 2009/0003524 | A1* | 1/2009 | Pu | 378/65 |
| 2009/0175418 | A1* | 7/2009 | Sakurai et al. | 378/98.5 |
| 2010/0202588 | A1 | 8/2010 | Shibuya et al. | |

FOREIGN PATENT DOCUMENTS

| | | | |
|---|---|---|---|
| JP | 2009-160309 | A | 7/2009 |
| JP | 2010-183976 | A | 8/2010 |
| WO | WO 2010/143266 | A1 | 12/2010 |
| WO | WO 2010/143267 | A1 | 12/2010 |

* cited by examiner

PARTICLE BEAM IRRADIATION APPARATUS, PARTICLE BEAM THERAPY SYSTEM, AND DATA DISPLAY PROGRAM

TECHNICAL FIELD

The present invention relates to a particle beam irradiation apparatus and a particle beam therapy system for performing treatment of a cancer or the like by use of a particle beam.

BACKGROUND ART

A particle beam therapy system is a medical apparatus for performing treatment by irradiating a charged particle beam onto a diseased site such as a cancer. The function, to be required, of a particle beam therapy system is to form an irradiation field in such a way as to provide a diseased site such as a cancer with a dose required for treatment and to provide other normal tissues with as few dose as possible. Irradiation field forming methods include the broad beam irradiation method and the scanning irradiation method.

In the broad beam irradiation method, at first, an irradiation field is enlarged by use of a scatterer or the like and then is formed to conform to a diseased site by use of a collimator, a bolus, or the like. Because its safety had been assured through clinical research, the broad beam irradiation method has most widely been adopted in a conventional particle beam therapy system. However, because the shape of a diseased site differs depending on a patient, or because even in a single and the same patient, a diseased site shrinks as a treatment proceeds, it is required to create a bolus each time the diseased site shrinks; therefore, there has been desired a more flexible irradiation field forming method. Accordingly, in recent years, there have actively been conducted R&Ds in which the scanning irradiation method is adopted in a particle beam therapy system.

The scanning irradiation method denotes a method in which a pencil-shaped thin charged particle beam is irradiated while being three-dimensionally scanned in such a way as to conform to the shape of a diseased site. The scanning irradiation method in which irradiation and non-irradiation of a pencil-shaped thin charged particle beam are alternatively repeated so that the pencil-shaped thin charged particle beam is irradiated in a spot shape and in a pointillism manner is referred to as the spot scanning method, in particular. The scanning irradiation method in which a pencil-shaped thin charged particle beam is scanned while being irradiated so that the pencil-shaped thin charged particle beam is irradiated in a one-stroke writing manner is referred to as the raster-scanning method, in particular. In each of the spot scanning method and the raster-scanning method, in order to scan a pencil-shaped thin charged particle beam, there is utilized an electromagnet, referred to as a scanning electromagnet or a "so-sa" electromagnet (referred to as a "scanning electromagnet", hereinafter), that makes a magnetic field change at high speed.

It goes without saying that in order to acquire high scanning accuracy of a scanning electromagnet, i.e., high irradiation accuracy of a particle beam therapy system, it is required to appropriately control the scanning electromagnet. However, the irradiation accuracy of a particle beam therapy system is deteriorated with time, even though the particle beam therapy system is adjusted at an initial stage. Accordingly, it is desirable to display the irradiation position accuracy in such a way that the tendency thereof is observed at a glance, so that the irradiation accuracy of the particle beam therapy system can appropriately be maintained and the maintenance thereof can be performed. Patent Document 1 discloses a charged particle beam irradiation system in which based on a detection signal from a position monitor, the deviation (the difference from the desired value) of a beam irradiation position is calculated; it is determined whether or not the calculated deviation of a beam irradiation position has exceeded an allowable value; for example, in the case where it is determined that the deviation of a beam irradiation position has exceeded the allowable value, an interlock signal and a display signal are outputted to an output unit; and then the beam irradiation is stopped.

PRIOR ART REFERENCE

Patent Document

[Patent Document 1] Japanese Patent Application Laid-Open No. 2009-39219 (Paragraphs 0043 and 0050)

DISCLOSURE OF THE INVENTION

Problems to be Solved by the Invention

The charged particle beam irradiation system disclosed in Patent Document 1 makes it possible that based on a detection signal from a position monitor, the deviation (the difference from the desired value) of a beam irradiation position is calculated; it is determined whether or not the calculated deviation of a beam irradiation position has exceeded an allowable value; then, in the case where it is determined that the deviation of a beam irradiation position has exceeded the allowable value, the beam irradiation is stopped. However, with regard to the foregoing charged particle beam irradiation system, there exists no method of displaying the accuracy of a charged particle beam irradiation position in such a way that the tendency thereof is observed at a glance, and the function therefor is not provided. In particular, in an apparatus of the type in which a beam is irradiated while being scanned, in terms of maintaining the irradiation accuracy and performing the maintenance, extremely important are that the irradiation position and the irradiation position error can be displayed in such a way as to correspond to each other and that the irradiation position relevant value related to the irradiation position and the irradiation position relevant value error can be displayed in such a way as to correspond to each other.

The "irradiation position relevant value related to the irradiation position" does not necessarily denote the irradiation position itself; it is a value that has a one-to-one relationship with the irradiation position and from which the irradiation position can be derived. For example, each of the output value of a position monitor, the output value of a magnetic-field sensor mounted on a scanning electromagnet, and the like corresponds to the irradiation position relevant value related to the irradiation position. Additionally, the irradiation position relevant value error denotes the error in the irradiation position relevant value with respect to a desired irradiation position relevant value. Here, even though the desired irradiation position relevant value does not necessarily denote the desired irradiation position itself, it is a value that has a one-to-one relationship with the desired irradiation position, because the desired irradiation position relevant value and the desired irradiation position are related to each other in the same manner as the irradiation position and the irradiation position relevant value are related to each other, and from which the desired irradiation position can be derived.

The present invention has been implemented for the purpose of solving the foregoing problems; the objective thereof is to provide a particle beam irradiation apparatus in which the irradiation position and the irradiation position error can be displayed in such a way as to correspond to each other or the irradiation position relevant value related to the irradiation position of a charged particle beam and the irradiation position relevant value error can be displayed in such a way as to correspond to each other.

Means for Solving the Problems

There are provided a detector that detects a measured irradiation position relevant value related to the irradiation position of a charged particle beam, and a data processing apparatus that displays on a display unit the measured irradiation position relevant value and an irradiation position relevant value error, which is an error of the measured irradiation position relative value with respect to a desired irradiation position relevant value related to a desired irradiation position of the charged particle beam, in such a way that the measured irradiation position relevant value and the irradiation position relevant value error correspond to each other. The data processing apparatus has an input unit that receives the measured irradiation position relevant value and the desired irradiation position relevant value; and a calculation unit that displays a desired value display figure indicating the desired irradiation position relevant value at the coordinates of the desired irradiation position relevant value and a measured value display figure indicating the measured irradiation position relevant value at display coordinates, which are coordinates obtained by adding the desired irradiation position relevant value to the coordinates acquired by arithmetically operating the irradiation position relevant value error with deformation coefficients, when the desired value display figure and the measured value display figure are displayed in a display region which is the reproduction of an irradiation-region relevant region related to an irradiation region of the charged particle beam, and that displays a line that connects the measured value display figure with the desired value display figure.

There are provided a detector that detects a measured irradiation position relevant value related to the irradiation position of a charged particle beam, and a data processing apparatus that calculates a measured irradiation position of the charged particle beam, based on the measured irradiation position relevant value, and displays on a display unit the measured irradiation position and an irradiation position error, which is the error of the measured irradiation position with respect to a desired irradiation position of the charged particle beam, in such a way that the measured irradiation position and the irradiation position error correspond to each other. The data processing apparatus has an input unit that receives the measured irradiation position relevant value and the desired irradiation position; and a calculation unit that displays a desired value display figure indicating the desired irradiation position at the coordinates of the desired irradiation position and a measured value display figure indicating the measured irradiation position at display coordinates, which are coordinates obtained by adding the desired irradiation position to the coordinates acquired by arithmetically operating the irradiation position error with deformation coefficients, when the desired value display figure and the measured value display figure are displayed in a display region which is the reproduction of an irradiation region of the charged particle beam, and that displays a line that connects the measured value display figure with the desired value display figure.

Advantage of the Invention

In a particle beam irradiation apparatus according to the present invention, the irradiation position accuracy of a charged particle beam can be displayed in such a way that the irradiation position relevant value related to the irradiation position and the irradiation position relevant value error correspond to each other. Moreover, the irradiation position accuracy of a charged particle beam can be displayed in such a way that the irradiation position and the irradiation position error correspond to each other. Therefore, the user can intuitively and easily understand the foregoing display, and can readily grasp the irradiation position accuracy displayed in such a way that the irradiation position relevant value related to the irradiation position of a charged particle beam and the irradiation position relevant value error correspond to each other and the irradiation position accuracy displayed in such a way that the measured irradiation position of the charged particle beam and the irradiation position error correspond to each other. As a result, it is made possible to appropriately maintain the irradiation position accuracy and to perform the maintenance.

BEST MODE FOR CARRYING OUT THE INVENTION

Embodiment 1

Figure 1:
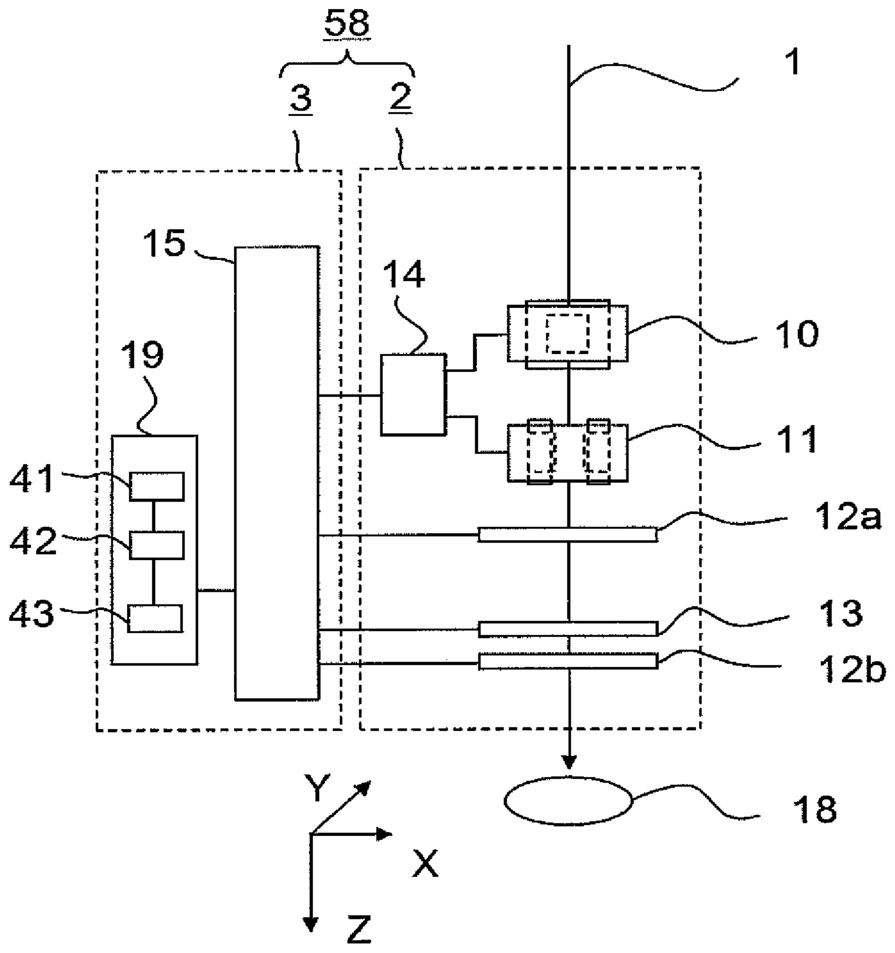
FIG. 1 is a schematic block diagram illustrating a particle beam irradiation apparatus according to Embodiment 1 of the present invention.

FIG. 1 is a schematic configuration diagram illustrating a particle beam irradiation apparatus according to Embodiment 1 of the present invention. A particle beam irradiation apparatus 58 has an irradiation apparatus unit 2 and a control/management unit 3 that controls and manages the irradiation apparatus unit 2. The irradiation apparatus unit 2 is provided with an X-direction scanning electromagnet 10 and a Y-direction scanning electromagnet 11 that scan a charged particle beam 1 in the X direction and the Y direction, respectively, which are directions perpendicular to the charged particle beam 1; an upstream-side position monitor 12*a*, a dose monitor 13, a downstream-side position monitor 12*b*, and a scanning electromagnet power source 14. The control/management unit 3 is provided with an irradiation control apparatus 15 that controls the irradiation apparatus unit 2 and a data processing apparatus 19. The traveling direction of the charged particle beam 1 is the Z direction.

The X-direction scanning electromagnet 10 is a scanning electromagnet that performs X-direction scanning with the charged particle beam 1; the Y-direction scanning electromagnet 11 is a scanning electromagnet that performs Y-direction scanning with the charged particle beam 1. The upstream-side position monitor 12*a* and the downstream-side position monitor 12*b* detect the beam peak position (passing position), of the beam, through which the charged particle beam 1 that has been scanned by the X-direction scanning electromagnet 10 and the Y-direction scanning electromagnet 11 passes. The dose monitor 13 detects the dose of the charged particle beam 1. The irradiation control apparatus 15 controls the irradiation position of the charged particle beam 1 on an irradiation subject 18, based on treatment plan data created by an unillustrated treatment planning apparatus; when the dose measured by the dose monitor 13 and converted into digital data reaches the desired dose, the charged particle beam 1 is stopped. The scanning electromagnet power source 14 changes setting currents for the X-direction scanning electromagnet 10 and the Y-direction scanning electromagnet 11, based on control inputs (command currents), which are outputted from the irradiation control apparatus 15, to the X-direction scanning electromagnet 10 and the Y-direction scanning electromagnet 11.

The data processing apparatus 19 displays, on a display region an irradiation region related to an irradiation region, the irradiation position (X, Y) of the charged particle beam 1 and an error at the irradiation position (X, Y) in such a way that they correspond to each other; alternatively, the data processing apparatus 19 displays, on a display region which is the reproduction of an irradiation-region relevant region related to the irradiation region, an irradiation position relevant value ($A_X$, $A_Y$) related to the irradiation position (X, Y) of the charged particle beam 1 and an error (irradiation position relevant value error ($E_X$, $E_Y$)) at the irradiation position relevant value in such a way that they correspond to each other. The irradiation position relevant value ($A_X$, $A_Y$)) includes a desired irradiation position relevant value ($A0_X$, $A0_Y$) related to a desired irradiation position (X0, Y0) and an measured irradiation position relevant value ($A1_X$, $A1_Y$) related to an measured irradiation position (X1, Y1), of the charged particle beam 1, measured by the position monitors 12*a* and 12*b* and calculated. The irradiation position relevant value error ($E_X$, $E_Y$) is a value obtained by subtracting the desired irradiation position relevant value ($A0_X$, $A0_Y$) from the measured irradiation position relevant value ($A1_X$, $A1_Y$). The irradiation-region relevant region related to the irradiation region is a position monitor value region obtained by two-dimensionally expressing the output values of the position monitors 12*a* and 12*b*. This embodiment will be explained by use of an irradiation region obtained by transforming the position monitor value region of the charged particle beam 1 into the irradiation position (X, Y) on the irradiation subject. The irradiation position, the desired irradiation position, the measured irradiation position, the positional error can paradoxically be expressed as follows: The irradiation position corresponds to information by converting the irradiation position relevant value. The desired irradiation position corresponds to information by converting the desired irradiation position relevant value. The measured irradiation position corresponds to information by converting the measured irradiation position relevant value. The positional error corresponds to information by converting the irradiation position relevant value error. Additionally, the irradiation-region relevant region, the irradiation position relevant value, the desired irradiation position relevant value, the measured irradiation position relevant value, and the irradiation position relevant value error are appropriately expressed with parentheses in such a way as to be attached to the corresponding phrases.

Figure 2:
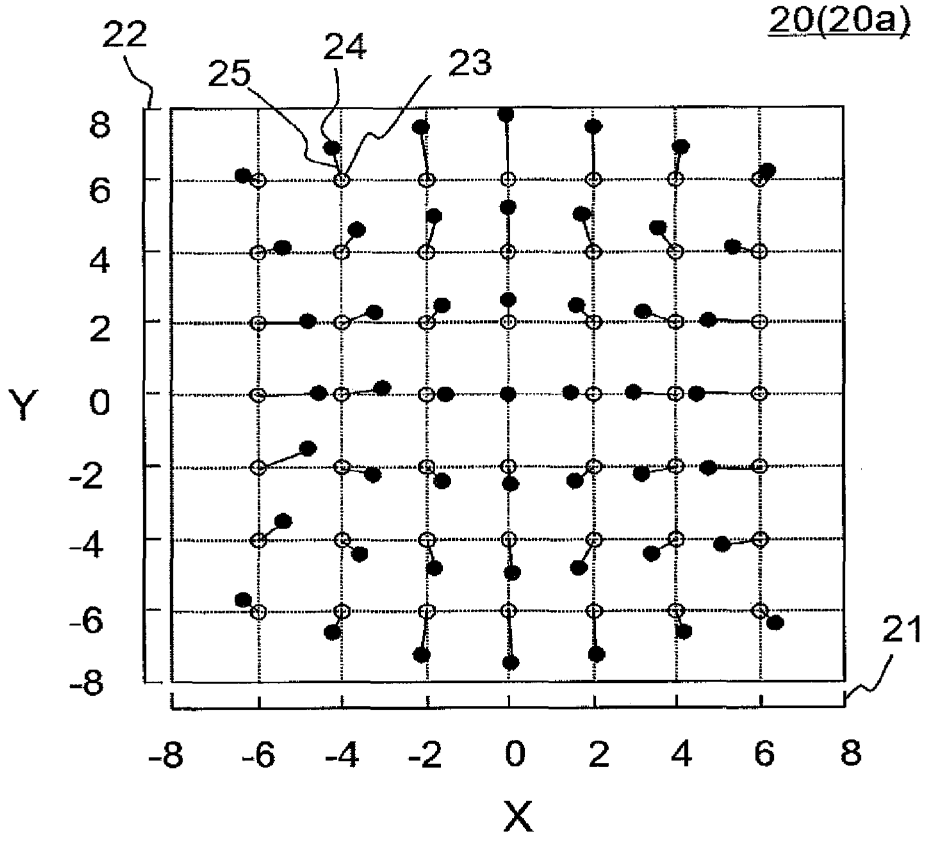
FIG. 2 is a chart representing a pincushion expression displayed by the data processing apparatus in FIG. 1.

As the data processing apparatus 19, dedicated hardware may be utilized; however, a universal personal computer or a workstation can also be utilized. In this embodiment, for easier understanding, there will be explained a case where a universal personal computer or a workstation is utilized. The data processing apparatus 19 has an input unit 41 to which the desired irradiation position (desired irradiation position relevant value) and the measured irradiation position (measured irradiation position relevant value) in the irradiation region (irradiation-region relevant region) are inputted, a display unit 43 that displays a reproduced irradiation region on a screen, and a calculation unit 42 that performs processing for displaying the reproduced irradiation region on the display unit 43. The data processing apparatus 19 has first through fourth functions; the result realized by these functions is represented in FIG. 2. FIG. 2 is a chart representing pincushion expression displayed by a data processing apparatus according to Embodiment 1 of the present invention. The definition and the like of the pincushion expression will be described later.

The first function of the data processing apparatus 19 is to reproduce and display the irradiation region (irradiation-region relevant region) of the charged particle beam 1 on the display unit screen of the data processing apparatus 19. The first function is implemented by a region display calculation unit in the calculation unit 42. In FIG. 2, the part, drawn by dotted lines in the shape of a lattice, in which graded scales are provided with an abscissa 21 (corresponding to the X direction) and an ordinate 22 (corresponding to the Y direction) corresponds to a display realized by the first function. It is desirable that the origin of pincushion expression 20 (20*a*) reproduced and displayed on the display unit screen corresponds to an isocenter, which is an irradiation reference. The X direction and the Y direction may be determined in an arbitrary manner in a particle beam therapy system; in general, the X-direction scanning electromagnet and the Y-direction scanning electromagnet are provided in such a way that the respective scanning directions of a beam coincide with the defined X direction and Y direction.

The second function of the data processing apparatus 19 is to display the desired irradiation position (desired irradiation position relevant value) in such a way that the desired irradiation position is superimposed on the irradiation region (irradiation-region relevant region) reproduced on the screen by the first function. The second function is implemented by a desired value calculation unit in the calculation unit 42. In FIG. 2, the plot of a circle that is not painted out, i.e., a circle 23 whose circumference is drawn by a solid line corresponds to a display realized by the second function. Additionally, in FIG. 2, the arrangement position of the circle 23 corresponds to the "desired position (the position that is stung with a pin: a desired value) of a "pin", described later. The circle 23 will be referred to as a desired irradiation position figure (desired value display figure) 23, as may be necessary.

The third function of the data processing apparatus 19 is to display the measured irradiation position (measured irradiation position relevant value) in such a way that the measured irradiation position is superimposed on the irradiation region (irradiation-region relevant region) reproduced on the screen by the first function and the desired irradiation position (desired irradiation position relevant value) superimposed on the irradiation region by the second function. The third function is implemented by a measured value calculation unit in the calculation unit 42. In FIG. 2, the plot of a circle 24 that is painted out corresponds to a display realized by the third function. Additionally, in FIG. 2, the arrangement position of the circle 24 corresponds to the "measured irradiation position (the pinhead: a measured value) of a "pin", described later. The circle 24 will be referred to as a measured irradiation position figure (measured value display figure) 24, as may be necessary. In the present invention, further contrivance is made to display the measured irradiation position (measured irradiation position relevant value). The further contrivance is that as the display of the measured irradiation position, the positional error (irradiation position relevant value error) at the measured irradiation position is deformed (changed by exaggerating or enhancing the characteristics) and displayed. The foregoing contrivance is represented by mathematical expressions.

Letting $P_{desired}$ denote the desired irradiation position, and $P_{measured}$ denote the measured irradiation position, the positional error $P_{error}$ can be given by the equation (1), and the measured irradiation position $P_{def}$ obtained by deforming the positional error can be given by the equation (2).

$$P_{error}=P_{measured}-P_{desired} \quad (1)$$

$$P_{def}=P_{desired}+k(P_{error}) \quad (2)$$

where k is a deformation coefficient. The desired irradiation position $P_{desired}$, the measured irradiation position $P_{measured}$, the measured irradiation position $P_{def}$ obtained by deforming the positional error, and the positional error $P_{error}$ are all expressed by vectors and indicate the respective coordinates in the irradiation region. The coordinates of the measured irradiation position $P_{def}$ calculated through the equation (2) are display coordinates when the measured irradiation position $P_{def}$ is displayed in a display region which is he reproduction of the irradiation region. With regard to the desired irradiation position relevant value, the measured irradiation position relevant value, the irradiation position relevant value error, and the deformed measured irradiation position relevant value, it is only necessary that they are expressed by $PR_{desired}$, $PR_{measured}$, $PR_{error}$, and $PR_{def}$, and in the equations (1) and (2), $P_{desired}$, $P_{measured}$, $P_{error}$, and $P_{def}$ are replaces by $PR_{desired}$, $PR_{measured}$, $PR_{error}$, and $PR_{def}$, respectively, i.e., by symbols with R. Hereinafter, a symbol with R suggests that it is related to an irradiation position relevant value.

Figure 3:
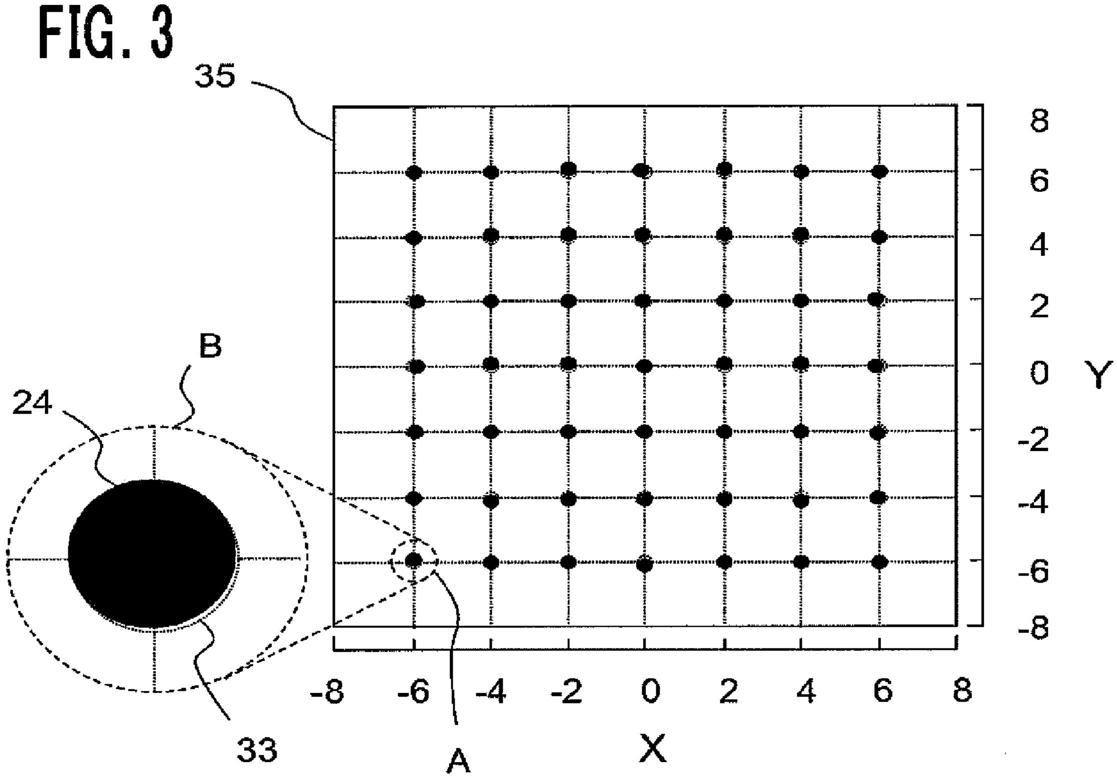
FIG. 3 is a chart representing an irradiation position in contrast to the pincushion expression in FIG. 2.

Assuming that the deformation coefficient k is "1", the measured irradiation position $P_{def}$ is not deformed; the arrangement position of the measured irradiation position figure 24 is displayed at an undeformed real measured irradiation position. Assuming that the deformation coefficient k is "0", the measured irradiation position $P_{def}$ is given a position corresponding to the desired irradiation position $P_{desired}$. In FIG. 2, each of a plurality of measured irradiation position figures 24 represents an example of measured irradiation position $P_{def}$ when it is assumed that the deformation coefficient k is "30". By plotting the measured irradiation positions $P_{def}$ without utilizing the deformation coefficient k, FIG. 3 is obtained. FIG. 3 is a chart representing an irradiation position in contrast to the pincushion expression 20 in FIG. 2. The part indicated by a dotted-line circle A in an irradiation position display 35 is an enlargement subject part, and the part represented by a dotted-line circle B is an enlarged enlargement subject part. The dotted-line circle 33 is a desired irradiation position figure and corresponds to the desired irradiation position figure 23 in FIG. 2. The desired irradiation position figure is represented by a dotted line so as to be distinguished from the measured irradiation position figure 24. The irradiation position error is small compared to the area of a display region which is the reproduction of the irradiation region in the irradiation position display 35; therefore, in general, without deforming the irradiation position error, it is difficult to determine the tendency thereof, as in FIG. 3.

The fourth function of the data processing apparatus 19 is to display the desired irradiation position $P_{desired}$ (desired irradiation position relevant value $PR_{desired}$), displayed by the second function, and the measured irradiation position $P_{def}$ (measured irradiation position relevant value $PR_{def}$), obtained by deforming the positional error $P_{error}$ (irradiation position relevant value error $PR_{error}$) displayed by the third function, that are connected with each other with a line. The fourth function is implemented by a line display calculation unit in the calculation unit 42. In FIG. 2, a line 25 corresponds to the expression realized by the fourth function. Additionally, the line 25 corresponds to the "pin body" of a "pin", described later. In the case where there exists the positional error $P_{error}$, the measured irradiation position $P_{def}$ obtained by deforming the positional error $P_{error}$ leaves rapidly the desired irradiation position $P_{desired}$, as the deformation coefficient k increases in the third function. Accordingly, the fourth function displays the desired irradiation position figure 23 indicating the desired irradiation position and the measured irradiation position figure 24 indicating the measured irradiation position that are connected with each other with the line 25, so that the relationship between then can easily be understood. It can be said that the third and fourth functions are special technical features in the present invention.

Here, the pin and the pincushion expression will be explained. In FIG. 2, the combination of the circle 24 that is painted out and the line 25 looks as if it were a pin (marking pin). The expression, represented in FIG. 2, on the display unit screen of the data processing apparatus 19 looks as if a pincushion are stung with pins; therefore, this expression is referred to as "pincushion expression" herein. Additionally, in contrast to the state where a pincushion is stung with pins, the desired irradiation position figure 23 in the pincushion expression 20, the measured irradiation position figure 24 (including both undeformed and deformed figures), and the line 25 that connects the desired irradiation position figure 23 with the measured irradiation position figure 24 correspond to a "position that is stung with a pin", a "pinhead", and a "pin body".

Because the particle beam irradiation apparatus 58 according to Embodiment 1 is provided with the data processing apparatus 19 having the four functions, the irradiation position accuracy of the charged particle beam 1 can be displayed in such a way that the irradiation position P and the irradiation position error $P_{error}$ correspond to each other. Additionally, the irradiation position accuracy of the charged particle beam 1 can be displayed in such a way that the irradiation position relevant value PR related to the irradiation position and the irradiation position relevant value error $PR_{error}$ correspond to each other. Therefore, the user can intuitively and easily understand the foregoing display, and can readily grasp the irradiation position accuracy displayed in such a way that the irradiation position P of the charged particle beam 1 and the irradiation position error $P_{error}$ correspond to each other and the irradiation position accuracy displayed in such a way that the irradiation position relevant value PR related to the irradiation position of the charged particle beam 1 and the irradiation position relevant value error $PR_{error}$ correspond to each other. As a result, it is made possible to appropriately maintain the irradiation position accuracy and to perform the maintenance.

Figure 4:
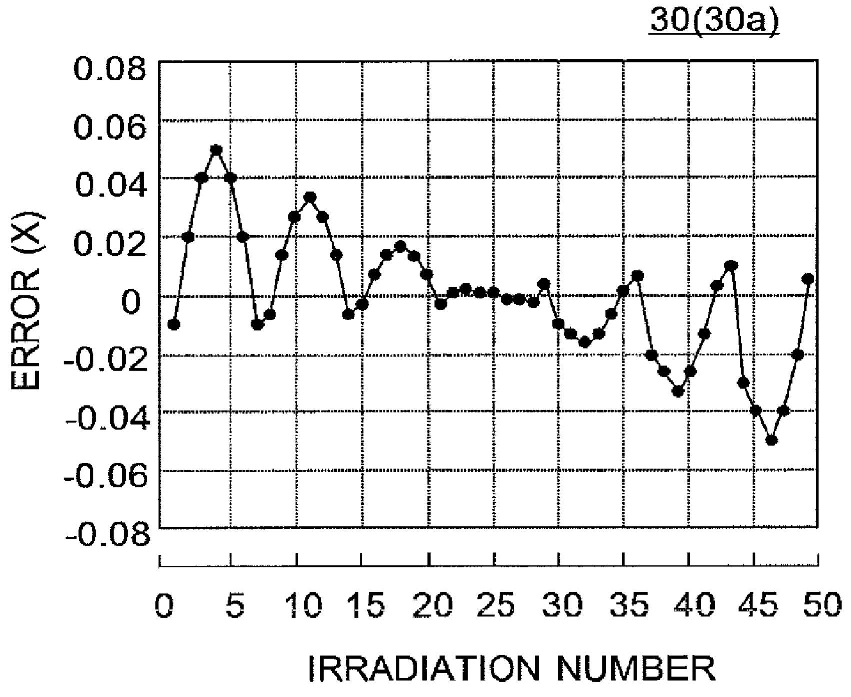
FIG. 4 is a chart representing a time-series expression of an X-direction error displayed by the data processing apparatus in FIG. 1.
Figure 5:
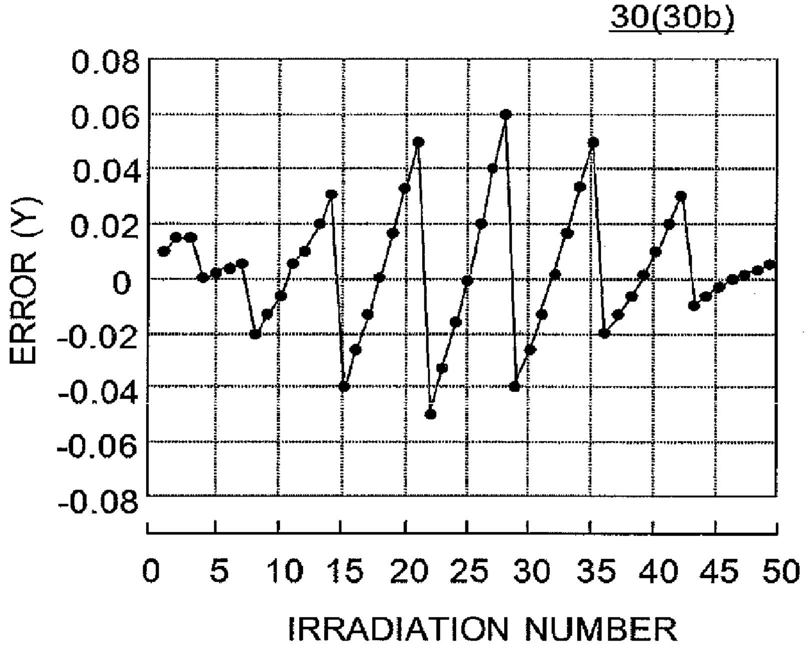
FIG. 5 is a chart representing a time-series expression of a Y-direction error displayed by the data processing apparatus in FIG. 1.

It may be allowed that on the display unit screen of the data processing apparatus 19, another display for supplementing the pincushion expression 20 is implemented. FIGS. 4 and 5 are graphs (referred to as "time-series expression", hereinafter) representing in a time-series manner the X-direction component and the Y-direction component, respectively, of the positional error. FIG. 4 is a graph representing the time-series expression 30 (30*a*) of the X-direction error; FIG. 5 is a graph representing the time-series expression 30 (30*b*) of the Y-direction error. The abscissa denotes the irradiation number indicating the order of irradiation of the charged particle beam 1; the ordinate denotes the error in the position (irradiation position relevant value). Data with larger irradiation number is more advanced in time than data with smaller irradiation number. Thus, the time-series expression (30*a*, 30*b*) gives effective information in the case where the positional error (irradiation position relevant value error) is analyzed in relation to the time. For example, there can readily be grasped information such as that the error has become large after the irradiation number "n" (the time tn).

Figure 6:
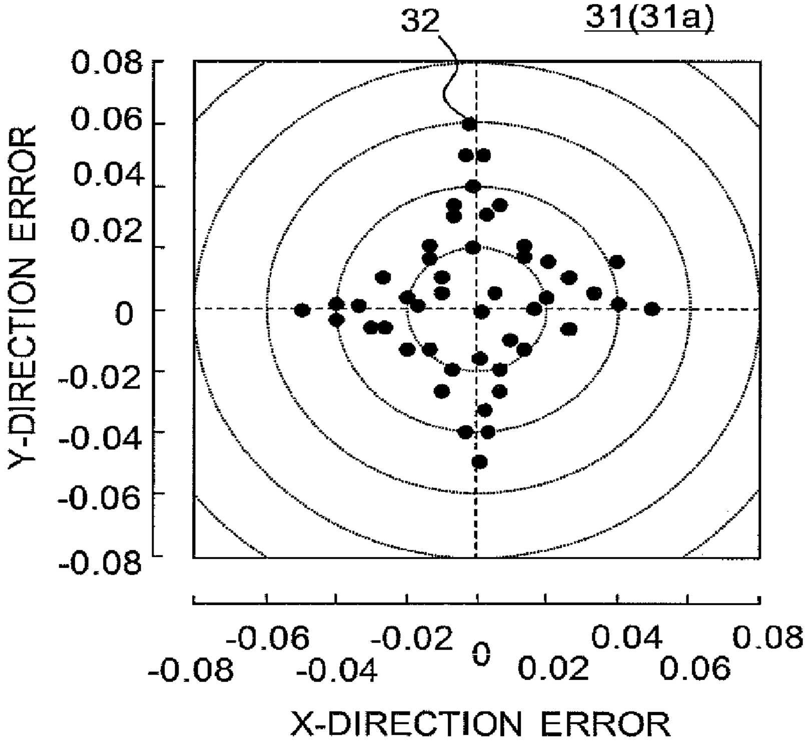
FIG. 6 is a chart representing error vector expression displayed by the data processing apparatus in FIG. 1.

In addition, it may be allowed that on the display unit screen of the data processing apparatus 19, another display for supplementing the pincushion expression 20 is implemented. FIG. 6 is a chart representing the vector expression of errors in the positions (irradiation position relevant values). Hereinafter, a chart in which errors are expressed in a vector manner will be referred to as "error vector expression", and a chart in which errors in the positions are expressed in a vector manner will be referred to as "positional error (irradiation position relevant value error) vector expression". The abscissa denotes the X-direction error; the ordinate denotes the Y-direction error. In an error vector expression 31, an error point 32 is displayed corresponding to the irradiation spot of the charged particle beam 1. Among the error vector expressions 31, which are expressions on such an error plane as in FIG. 6, the error vector expression 31 of a positional error is distinguished as a positional error vector expression 31*a*. The error vector expression 31 is the most effective expression method in the case where it is determined whether or not actual irradiation is being implemented within the allowable error range of the particle beam irradiation apparatus 58. In the error vector expression 31, by further displaying a border line indicating the boundary of the allowable error range, it can readily be determined whether or not actual irradiation has been implemented within the allowable error range.

Measured irradiation position relative data, which is data for creating the pincushion expression 20, the time-series expression 30, and the error vector expression 31, is obtained not only during irradiation of the charged particle beam 1 but also during particle-beam therapy. The measured irradiation position relative data is data related to the measured irradiation position of the charged particle beam 1. In Embodiment 1, the measured irradiation position relative data is the data on the position, of the charged particle beam 1, detected and calculated by the position monitors 12*a* and 12*b*. The measured irradiation position relative data may be the data on the magnetic field, of the charged particle beam 1, detected by magnetic-field sensors 8 and 9 (refer to FIG. 9).

Additionally, the measured irradiation position relative data may not be the position data of the charged particle beam 1 that has passed through the position monitor 12*a* or 12*b*, but be the position data of the charged particle beam 1 on a given reference plane. For example, it may be allowed that as the reference plane, there is adopted a slicing plane obtained by slicing the irradiation subject 18, and that as measured irradiation position relative data, there is adopted the position data of the charged particle beam 1 on the slicing plane.

The pincushion expression 20, the time-series expression 30, and the error vector expression 31 can be displayed not only during irradiation (online display) but also at an arbitrary time after irradiation (offline display). In the case where there is limited the capacity of a memory for storing the measured irradiation position relative data, the data may be obtained, for example, at the time of a specific event such as calibration conducted first thing in the morning of a day when the particle beam irradiation apparatus 58 is operated or the first therapy of the day. Even in the case where an error is produces in the measurement data, an allowable range exists for the error; therefore, even in the case where the data is obtained at the time of a specific event, there can be determined the timing when the maintenance is implemented.

The pincushion expression 20, the time-series expression 30, and the error vector expression 31 can be utilized also in setting and calibrating the particle beam irradiation apparatus 58. In particular, the online display is effective. Also in this case, the irradiation position accuracy of the charged particle beam 1 can be displayed in such a way that the irradiation position P and the irradiation position error $P_{error}$ correspond to each other. Additionally, the irradiation position accuracy of the charged particle beam 1 can be displayed in such a way that the irradiation position relevant value PR related to the irradiation position and the irradiation position relevant value error $PR_{error}$ correspond to each other. Accordingly, there can readily be made consideration about the plan of adjustment in performing setting, i.e., as to in which direction (the X direction or the Y direction) and how much correction is implemented.

In the offline display, for example, three-day data pieces are displayed in a superimposed manner, whereby a change in the error can be viewed. By superimposing and displaying data on the reference day, the difference with respect to the reference day can be viewed. It is made possible to determine the maintenance timing through viewing the change in the error or the difference with respect to the reference day.

The input value to the deformation coefficient k is selected for each apparatus. In general, the error is proportional to the size of the electromagnet. Additionally, the error is proportional to the distance between the electromagnet and the irradiation subject. In the case where the difference between the measured irradiation position $P_{measured}$ (measured irradiation position relevant value $PR_{measured}$) and the desired irradiation position $P_{desired}$ (desired irradiation position relevant value $PR_{desired}$) can clearly be seen, the deformation may not be implemented, i.e., the deformation coefficient k may be set to "1". In the case where the error is extremely small, by setting the deformation coefficient k to a large value, the irradiation position accuracy can readily be grasped. Additionally, the default value of the deformation coefficient may be set to a value that has been utilized last time or "1". By utilizing the default value, it is made possible that pincushion expression can be implemented without inputting the deformation coefficient from outside.

As described above, in the particle beam irradiation system 58 according to Embodiment 1, there are provided the detectors 12*a* and 12*b* that detect the measured irradiation position relevant value $PR_{measured}$ related to the irradiation position of the charged particle beam 1, and the data processing apparatus 19 that displays on the display unit 43 the measured irradiation position relevant value $PR_{measured}$ and the irradiation position relevant value error $PR_{error}$, which is the error of the measured irradiation position relevant value $PR_{measured}$ with respect to the desired irradiation position relevant value $PR_{desired}$ related to the desired irradiation position of the charged particle beam 1, in such a way that the measured irradiation position relevant value $PR_{measured}$ and the irradiation position relevant value error $PR_{error}$ correspond to each other; and the data processing apparatus 19 has the input unit 41 to which the measured irradiation position relevant value $PR_{measured}$ and the desired irradiation position relevant value $PR_{desired}$ are inputted, and the calculation unit 42 that displays the desired value display figure 23 at the coordinates of the desired irradiation position relevant value $PR_{desired}$ and the measured value display figure 24 at the display coordinates $PR_{def}$, which are coordinates obtained by adding the desired irradiation position relevant value $PR_{desired}$ to the coordinates acquired by arithmetically operating the irradiation position relevant value error $PR_{error}$ with the deformation coefficient k, when the desired value display figure 23 indicating the desired irradiation position relevant value $PR_{desired}$ and the measured value display figure 24 indicating the measured irradiation position relevant value $PR_{measured}$ are displayed in a display region which is the reproduction of the irradiation-region relevant region related to the irradiation region of the charged particle beam 1, and that displays the line 25 that connects the measured value display figure 24 with the desired value display figure 23. Therefore, the irradiation position accuracy of the charged particle beam 1 can be displayed in such a way that the irradiation position relevant value PR related to the irradiation position and the irradiation position relevant value error $PR_{error}$ correspond to each other. Therefore, the user can intuitively and easily understand the foregoing display, and can readily grasp the irradiation position accuracy displayed in such a way that the irradiation position relevant value PR related to the irradiation position of the charged particle beam 1 and the irradiation position relevant value error $PR_{error}$ correspond to each other. As a result, it is made possible to appropriately maintain the irradiation position accuracy and to perform the maintenance.

Moreover, in the particle beam irradiation apparatus 58 according to Embodiment 1, there are provided the detectors 12*a* and 12*b* that detect the measured irradiation position relevant value $PR_{measured}$ related to the irradiation position of the charged particle beam 1, and the data processing apparatus 19 that calculates the measured irradiation position $P_{measured}$ of the charged particle beam 1, based on the measured irradiation position relevant value $PR_{measured}$, and displays on the display unit 43 the measured irradiation position $P_{measured}$ and the irradiation position error $P_{error}$, which is the error of the measured irradiation position $P_{measured}$ with respect to the desired irradiation position of the charged particle beam 1, in such a way that the measured irradiation position $P_{measured}$ and the irradiation position error $P_{error}$ correspond to each other; and the data processing apparatus 19 has the input unit 41 to which the measured irradiation position relevant value $PR_{measured}$ and the desired irradiation position $P_{desired}$ are inputted, and the calculation unit 42 that displays the desired value display figure 23 at the coordinates of the desired irradiation position $P_{desired}$ and the measured value display figure 24 at the display coordinates $P_{def}$, which are coordinates obtained by adding the desired irradiation position $P_{desired}$ to the coordinates acquired by arithmetically operating the irradiation position error $P_{error}$ with the deformation coefficient k, when the desired value display figure 23 indicating the desired irradiation position $P_{desired}$ and the measured value display figure 24 indicating the measured irradiation position $P_{measured}$ are displayed in a display region which is the reproduction of the irradiation region of the charged particle beam 1, and that displays the line 25 that connects the measured value display figure 24 with the desired value display figure 23. Therefore, the irradiation position accuracy of the charged particle beam 1 can be displayed in such a way that the irradiation position P and the irradiation position error $P_{error}$ correspond to each other. Accordingly, the user can intuitively and easily understand the foregoing display, and can readily grasp the irradiation position accuracy displayed in such a way that the irradiation position P of the charged particle beam 1 and the irradiation position error $P_{error}$ correspond to each other. As a result, it is made possible to appropriately maintain the irradiation position accuracy and to perform the maintenance.

Embodiment 2

Figure 7:
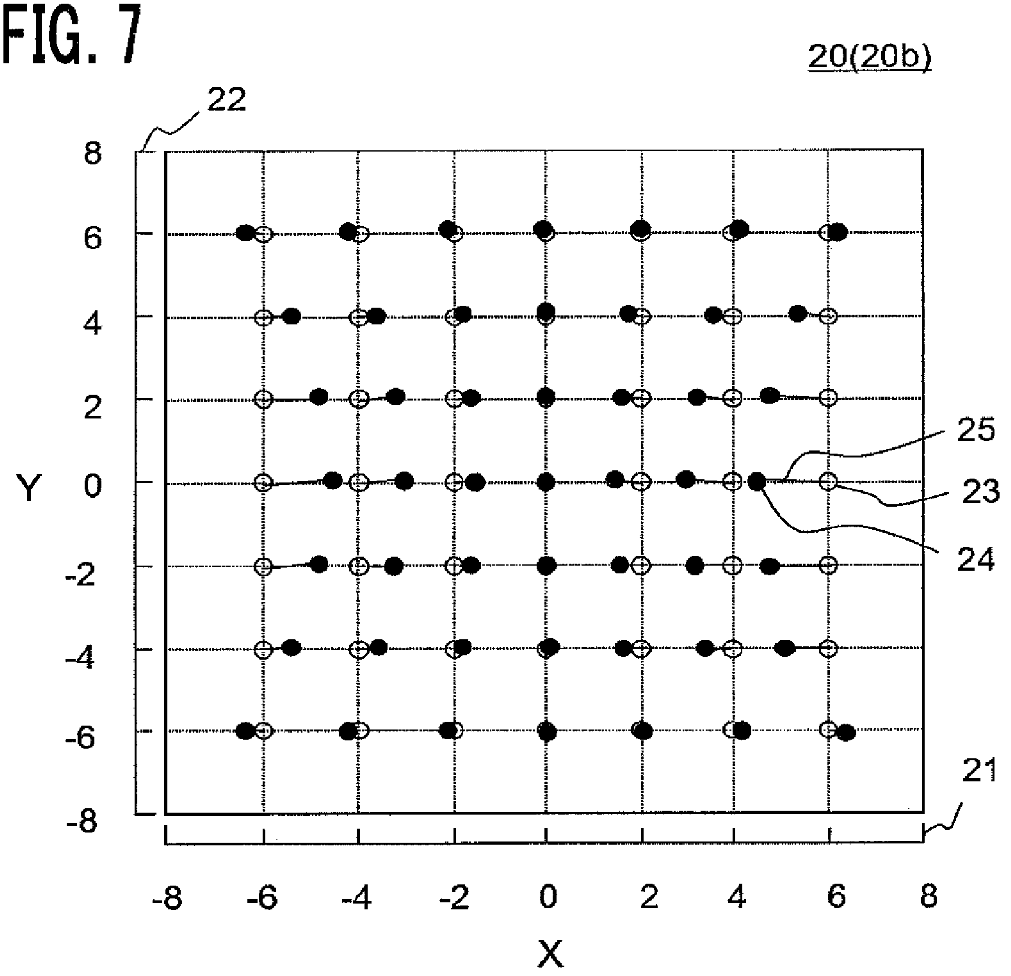
FIG. 7 is a chart representing first pincushion expression according to Embodiment 2 of the present invention.
Figure 8:
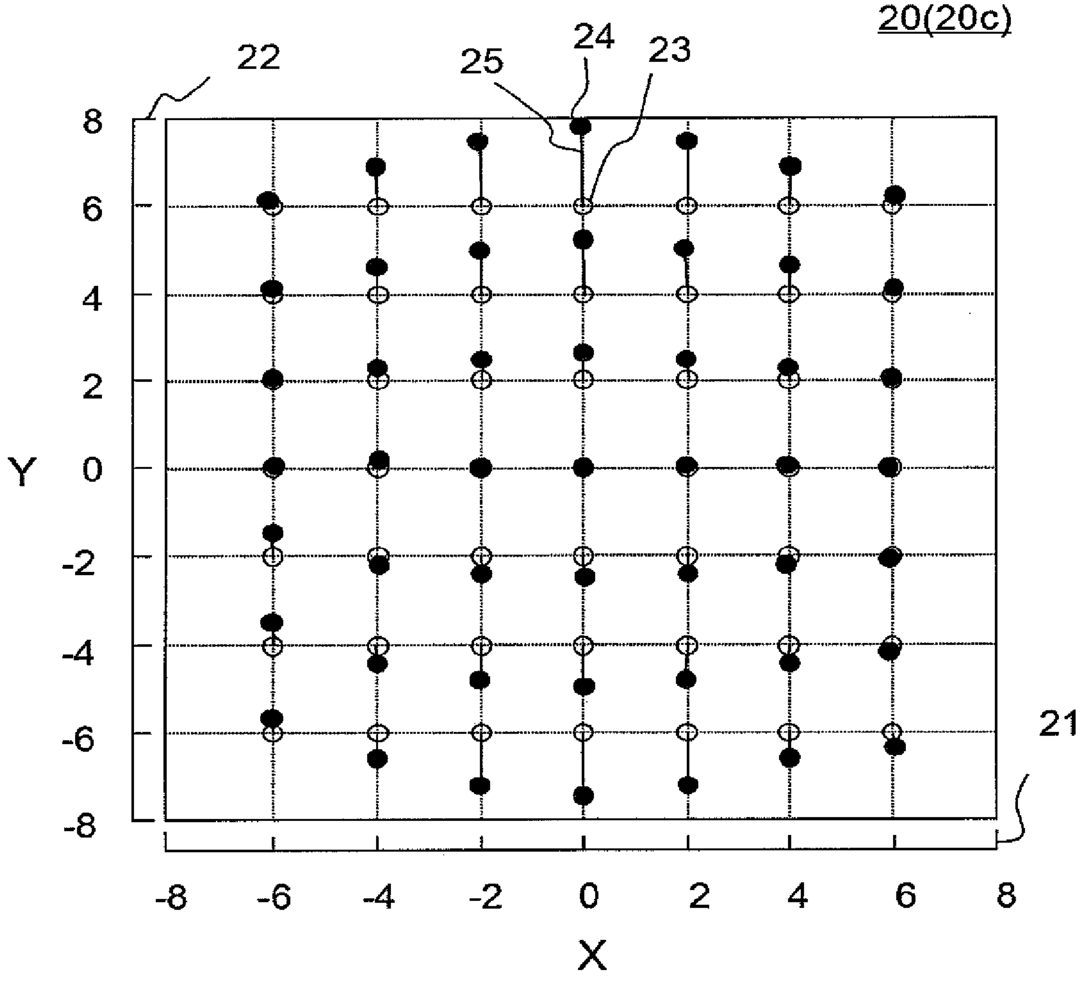
FIG. 8 is a chart representing second pincushion expression according to Embodiment 2 of the present invention.

In Embodiment 1, the equation (2), which is a basis of pincushion expression, has been proposed, and a notion "deformation coefficient" has been introduced. In Embodiment 2, there will be described a method in which respective deformation coefficients for the X-direction component and the Y-direction component are provided. FIG. 7 is a chart representing first pincushion expression according to Embodiment 2 of the present invention; FIG. 8 is a chart representing second pincushion expression according to Embodiment 2 of the present invention. FIG. 7 is an example representing pincushion expression 20 (20*b*) in the case where the X-direction deformation is of magnification "30" and the Y-direction deformation is of magnification "1". FIG. 8 is an example representing pincushion expression 20 (20*c*) in the case where the X-direction deformation is of magnification "1" and the Y-direction deformation is of magnification "30".

In the case where the respective deformation coefficients for X direction and Y direction are provided, the positional error $P_{error}$ can be given by the equation (5), and the measured irradiation position $P_{def}$ obtained by deforming the positional error can be given by the equation (6). As explained in Embodiment 1, the desired irradiation position $P_{desired}$, the measured irradiation position $P_{measured}$, the measured irradiation position $P_{def}$ obtained by deforming the positional error, and the positional error $P_{error}$ are all expressed by vectors. With regard to the desired irradiation position relevant value, the measured irradiation position relevant value, the irradiation position relevant value error, and the deformed measured irradiation position relevant value, it is only necessary to replace the foregoing symbols $P_{desired}$, $P_{measured}$, $P_{def}$, and $P_{error}$ by respective symbols with "R".

$$P_{desired} = \begin{bmatrix} p_{desired\_x} \\ p_{desired\_y} \end{bmatrix} \tag{3}$$

$$P_{measure} = \begin{bmatrix} p_{\_x} \\ p_{\_y} \end{bmatrix} \tag{4}$$

$$\begin{aligned} P_{error} &= P_{measured} - P_{desired} \\ &= \begin{bmatrix} p_{desired\_x} \\ p_{desired\_y} \end{bmatrix} - \begin{bmatrix} p_{\_x} \\ p_{\_y} \end{bmatrix} =: \begin{bmatrix} p_{error\_x} \\ p_{error\_y} \end{bmatrix} \end{aligned} \tag{5}$$

$$\begin{aligned} P_{def} &= P_{desired} + K(P_{error}) \\ &= \begin{bmatrix} p_{desired\_x} \\ p_{desired\_y} \end{bmatrix} + \begin{bmatrix} k_{\_x} & 0 \\ 0 & k_{\_y} \end{bmatrix} \begin{bmatrix} p_{error\_x} \\ p_{error\_y} \end{bmatrix} \\ &=: \begin{bmatrix} p_{def\_x} \\ p_{def\_y} \end{bmatrix} \end{aligned} \tag{6}$$

where "K" denotes a deformation coefficient matrix, and $k_{\_x}$ and $k_{\_y}$ denote an X-direction deformation coefficient and a Y-direction deformation coefficient, respectively.

The effect of the method in which the respective deformation coefficients for X direction and Y direction are provided is demonstrated in that because the scanning electromagnets 10 and 11 for scanning the charged particle beam 1 are separated from each other for the X direction and the Y direction, the tendencies of the X-direction and the Y-direction positional error $P_{error}$ (irradiation position relevant value error $PR_{error}$) can be viewed separately.

Because as is the case with Embodiment 1, the particle beam irradiation apparatus 58 according to Embodiment 2 is provided with the data processing apparatus 19 having the four functions, the irradiation position accuracy of the charged particle beam 1 can be displayed in such a way that the irradiation position P and the irradiation position error $P_{error}$ correspond to each other. Additionally, the irradiation position accuracy of the charged particle beam 1 can be displayed in such a way that the irradiation position relevant value PR related to the irradiation position and the irradiation position relevant value error $PR_{error}$ correspond to each other. Therefore, the user can intuitively and easily understand the foregoing display, and can readily grasp the irradiation position accuracy displayed in such a way that the irradiation position P of the charged particle beam 1 and the irradiation position error $P_{error}$ correspond to each other and the irradiation position accuracy displayed in such a way that the irradiation position relevant value PR related to the irradiation position of the charged particle beam 1 and the irradiation position relevant value error $PR_{error}$ correspond to each other. As a result, it is made possible to appropriately maintain the irradiation position accuracy and to perform the maintenance. In addition, the respective tendencies of the X-direction and the Y-direction positional error $P_{error}$ (irradiation position relevant value error $PR_{error}$) can separately be viewed; thus, there can readily be made consideration as to in which direction (the X direction or the Y direction) and how much correction is implemented.

Additionally, it may be allowed that on the display unit screen of the data processing apparatus 19, other expressions for supplementing the pincushion expression 20, i.e., as is the case with Embodiment 1, the X-direction error time-series expression 30 (30*a*), the Y-direction error time-series expression 30 (30*b*), and the error vector expression 31 are concurrently implemented.

Embodiment 3

In Embodiment 1, there has been explained a case where as examples of the irradiation position relevant value ($A_X$, $A_Y$), PR, and the irradiation position relevant value error ($E_X$, $E_Y$), $PR_{error}$, the output values of the position monitors 12*a* and 12*b* are utilized. In Embodiment 3, there will be explained a case where as examples of the irradiation position relevant value ($A_X$, $A_Y$), PR, and the irradiation position relevant value error ($E_X$, $E_Y$), $PR_{error}$, the output values of the magnetic-field sensors are utilized. The charged particle beam 1 is deflected by the X-direction scanning electromagnet 10 and the Y-direction scanning electromagnet 11 so as to be scanned on the irradiation subject 18. In other words, magnetic fields generated by the X-direction scanning electromagnet 10 and the Y-direction scanning electromagnet 11 controls the irradiation position (X, Y), P of the charged particle beam 1. Accordingly, the magnetic fields generated by the X-direction scanning electromagnet 10 and the Y-direction scanning electromagnet 11 are related to the irradiation position (X, Y), P. The irradiation-region relevant region related to an irradiation region is a magnetic field region.

Figure 9:
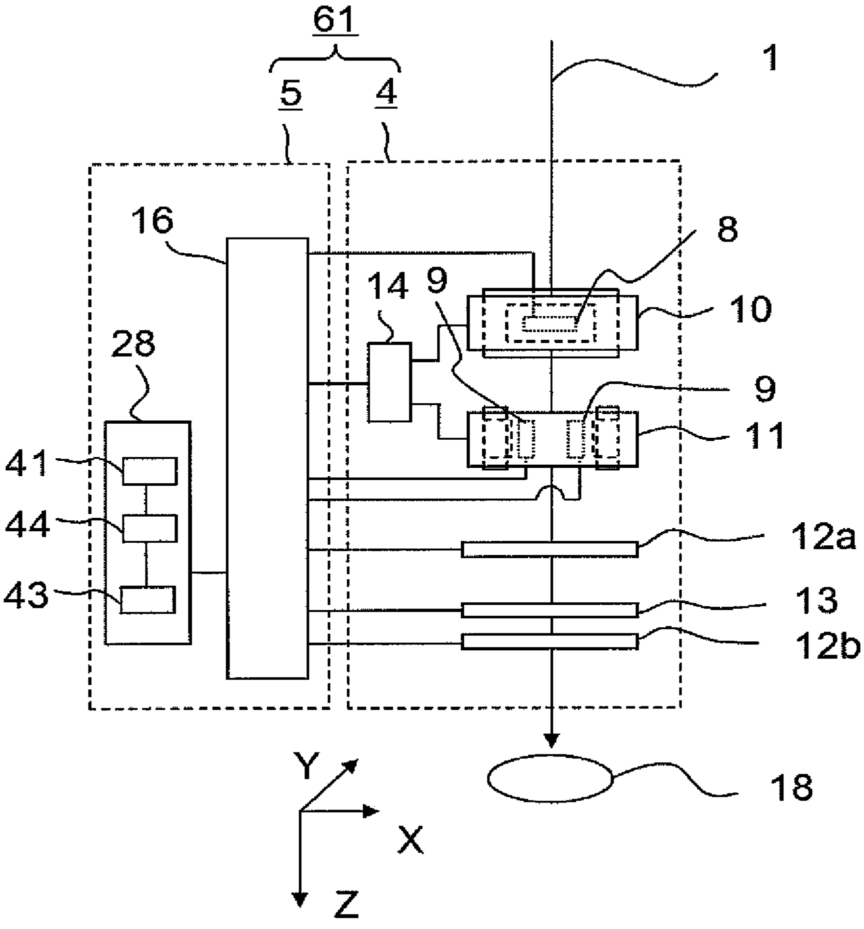
FIG. 9 is a schematic block diagram illustrating a particle beam irradiation apparatus according to Embodiment 3 of the present invention.

FIG. 9 is a schematic configuration diagram illustrating a particle beam irradiation apparatus according to Embodiment 3 of the present invention. Because being provided with an irradiation apparatus unit 4 having magnetic-field sensors 8 and 9 and a control/management unit 5 that processes data on magnetic fields, of the charged particle beam 1, detected by the magnetic-field sensors 8 and 9 and controls an irradiation apparatus unit 4, a particle beam irradiation apparatus 61 according to Embodiment 3 is different from the particle beam irradiation apparatus 58 according to Embodiment 1.

Figure 10:
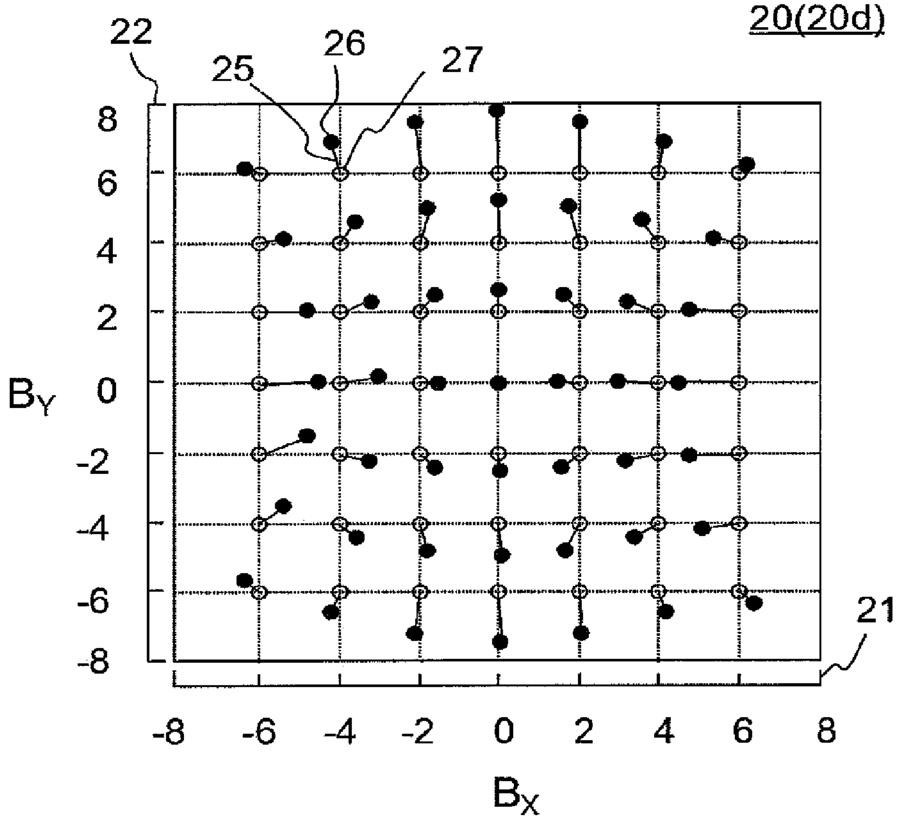
FIG. 10 is a chart representing a pincushion expression displayed by the data processing apparatus in FIG. 9.

The magnetic-field sensor 8 detects the magnetic field of the X-direction scanning electromagnet 10, and the magnetic-field sensor 9 detects the magnetic field of the Y-direction scanning electromagnet 11. The control/management unit 5 is provided with an irradiation control apparatus 16 that controls the irradiation apparatus unit 4 and a data processing apparatus 28. The data processing apparatus 28 has the input unit 41, a calculation unit 44, and the display unit 43. In Embodiment 3, the irradiation-region relevant region is expressed by a magnetic-field space. A desired magnetic field $B_{desired}$ in the irradiation-region relevant region and a measured magnetic field $B_{measured}$, which is an actually measured magnetic field, are inputted to the input unit 41. The display unit 43 reproduces and displays the irradiation-region relevant region on a screen. The calculation unit 44 performs processing for displaying on the display unit 43. The data processing apparatus 28 has the same first through fourth functions as in Embodiment 1; the result realized by these functions is represented in FIG. 10. FIG. 10 is a chart representing pincushion expression 20 (20*d*) displayed by a data processing apparatus according to Embodiment 3 of the present invention.

In FIG. 10, the abscissa 21 denotes an X-direction magnetic field $B_X$, and the ordinate 22 denotes a Y-direction magnetic field $B_Y$. As is the case with Embodiment 1, a circle 27, which is a desired value display figure, and a circle 26, which is a measured value display figure, are displayed in such a way as to be connected with each other with the line 25. In a display region which is the reproduction of a magnetic field, the circle 27, which is a desired value display figure, and the circle 26, which is a measured value display figure, can be referred to as a desired magnetic-field display figure and a measured magnetic-field figure, respectively. The circles 26 and 27 will be referred to as the desired magnetic-field display figure and the measured magnetic-field figure, respectively, as may be necessary.

The first function of the data processing apparatus 28 is to reproduce and display the magnetic-field region of the charged particle beam 1 on the display unit screen of the data processing apparatus 28. The first function is implemented by a region display calculation unit in the calculation unit 44.

The second function of the data processing apparatus 28 is to display the desired magnetic field $B_{desired}$ (desired irradiation position relevant value) in such a way that the desired magnetic field $B_{desired}$ is superimposed on the magnetic-field region reproduced on the screen by the first function. The second function is implemented by a desired value calculation unit in the calculation unit 44.

The third function of the data processing apparatus 28 is to display the measured magnetic field $B_{measured}$ (measured irradiation position relevant value) in such a way that the measured magnetic field $B_{measured}$ is superimposed on the magnetic-field region reproduced on the screen by the first function and the desired magnetic field $B_{desired}$ superimposed on the magnetic-field region by the second function. The third function is implemented by a measured value calculation unit in the calculation unit 44. As the expression of the measured magnetic field $B_{measured}$, the magnetic-field error $B_{error}$ (irradiation position relevant value error) at the measured magnetic field $B_{measured}$ is deformed and displayed. The foregoing description is represented by mathematical expressions as follows:

The magnetic-field error $B_{error}$ can be given by the equation (7), and the measured magnetic field $B_{def}$ obtained by deforming the magnetic-field error can be given by the equation (8).

$$B_{error}=B_{measured}-B_{desired} \quad (7)$$

$$B_{def}=B_{desired}+k(B_{error}) \quad (8)$$

where k is a deformation coefficient. The desired magnetic field $B_{desired}$, the measured magnetic field $B_{measured}$, the measured magnetic field $B_{def}$ obtained by deforming the magnetic-field error, and the magnetic-field error $B_{error}$ are all expressed by vectors and indicate the respective coordinates in the irradiation-region relevant region. The coordinates of the measured magnetic field $B_{def}$ calculated through the equation (8) are display coordinates when the measured magnetic field $B_{def}$ is displayed in a display region which is the reproduction of the irradiation-region relevant region.

The fourth function of the data processing apparatus 28 is to display the desired magnetic field $B_{desired}$, displayed by the second function, and the measured magnetic field $B_{def}$, obtained by deforming the magnetic-field error $B_{error}$ displayed by the third function, that are connected with each other with a line. The fourth function is implemented by a line display calculation unit in the calculation unit 44.

Because the particle beam irradiation apparatus 61 according to Embodiment 3 is provided with the data processing apparatus 28 having the four functions, the irradiation position accuracy of the charged particle beam 1 can be displayed in such a way that the magnetic field ($B_X$, $B_Y$), which is the irradiation position relevant value PR related to the irradiation position P, and the magnetic-field error $B_{error}$, which is the irradiation position relevant value error $PR_{error}$, correspond to each other. Therefore, the user can intuitively and easily understand the foregoing display, and can readily grasp the irradiation position accuracy displayed in such a way that the irradiation position relevant value PR related to the irradiation position P of the charged particle beam 1 and the irradiation position relevant value error $PR_{error}$ correspond to each other. As a result, it is made possible to appropriately maintain the irradiation position accuracy and to perform the maintenance.

Additionally, the irradiation position accuracy is grasped through the magnetic field; therefore, without actually irradiating the charged particle beam 1, the magnetic field can be measured by driving the X-direction scanning electromagnet 10 and the Y-direction scanning electromagnet 11. In the case where the charged particle beam 1 is not actually irradiated, the accelerator and the like need not to be operated; thus, the maintenance can be performed without preparing for the accelerator and the like, whereby the maintenance of the particle beam irradiation apparatus can be performed in a short time. Moreover, even when the maintenance of the accelerator and the like is being performed, the maintenance of the particle beam irradiation apparatus can be performed.

Figure 11:
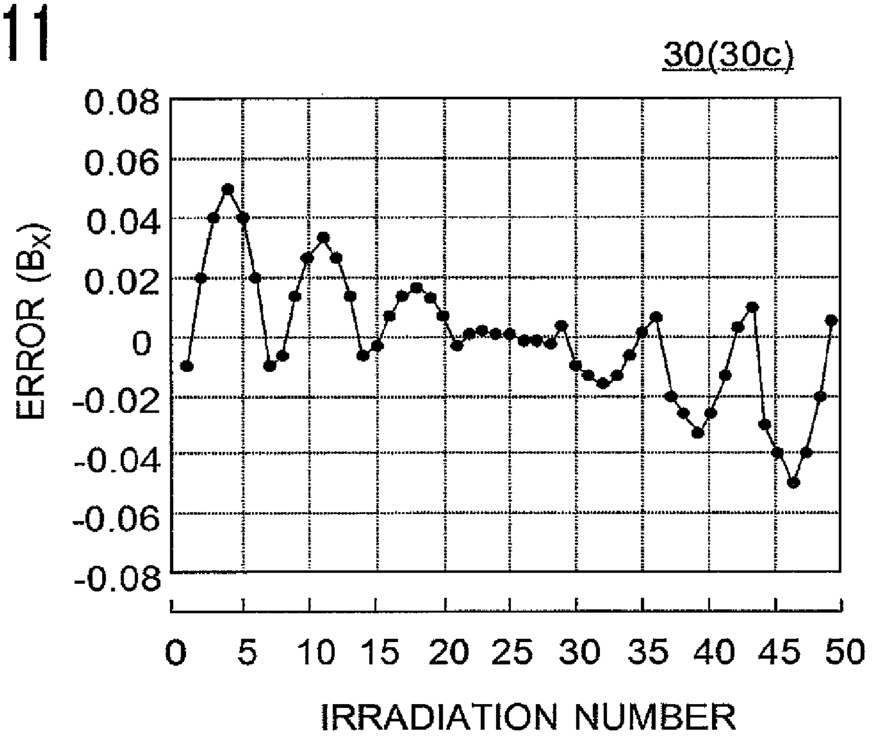
FIG. 11 is a chart representing a time-series expression of an X-direction error displayed by the data processing apparatus in FIG. 9.
Figure 12:
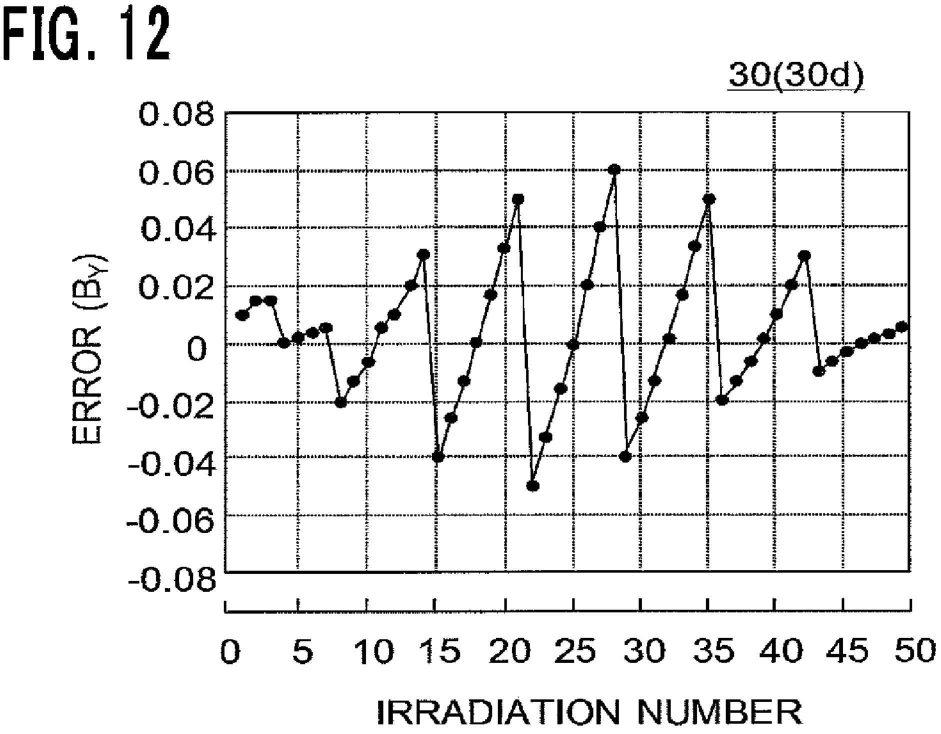
FIG. 12 is a chart representing a time-series expression of a Y-direction error displayed by the data processing apparatus in FIG. 9.

It may be allowed that on the display unit screen of the data processing apparatus 28, another display for supplementing the pincushion expression 20 is implemented. FIGS. 11 and 12 are each time-series expression representing in a time-series manner the X-direction component and the Y-direction component, respectively, of the magnetic-field error. FIG. 11 is a graph representing the time-series expression 30 (30*c*) of the X-direction error; FIG. 12 is a graph representing the time-series expression 30 (30*d*) of the Y-direction error. The abscissa denotes the irradiation number indicating the order according to which the irradiation of the charged particle beam 1 has been implemented or the order of irradiation to be implemented; the ordinate denotes the error in the magnetic field. Data with larger irradiation number is more advanced in time than data with smaller irradiation number. Thus, the time-series expression 30 (30*c*, 30*d*) gives effective information in the case where the magnetic-field error is analyzed in relation to the time. For example, there can readily be grasped information such as that the error has become large after the irradiation number "n" (the time tn).

Figure 13:
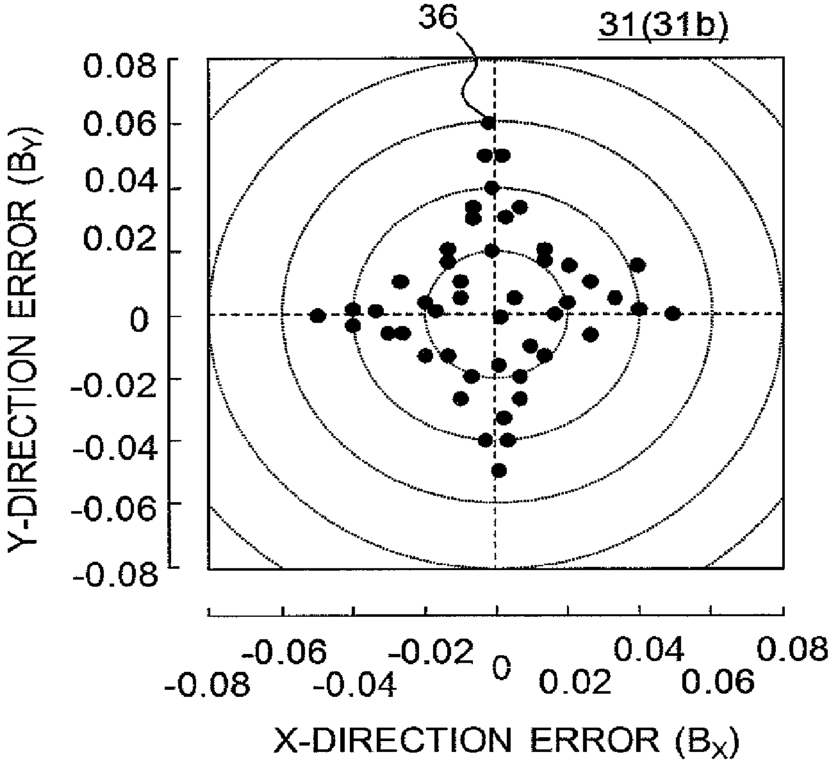
FIG. 13 is a chart representing error vector expression displayed by the data processing apparatus in FIG. 9.

In addition, it may be allowed that on the display unit screen of the data processing apparatus 28, another display for supplementing the pincushion expression 20 is implemented. FIG. 13 is a chart representing the vector expression of errors in the magnetic fields. A chart representing the vector expression of errors in the magnetic fields will be referred to as "magnetic-field error vector expression". The abscissa denotes the X-direction error; the ordinate denotes the Y-direction error. In an error vector expression 31 (31*b*), an error point 36 is displayed corresponding to the irradiation spot of the charged particle beam 1. The error vector expression 31 (31*b*) is the most effective expression method in the case where it is determined whether or not irradiation has actually been implemented or irradiation can be implemented within the allowable error range of the particle beam irradiation apparatus 61. In the error vector expression 31 (31*b*), by further displaying a border line indicating the boundary of the allowable error range, it can readily be determined whether or not actual irradiation has been implemented within the allowable error range.

As is the case with Embodiment 1, the pincushion expression 20, the time-series expression 30, and the error vector expression 31 can be displayed not only during irradiation (online display) but also at an arbitrary time after irradiation (offline display).

In addition, the data processing apparatus 28 may the type, described in each of Embodiments 1 and 2, that displays the pincushion expression 20 (20*a*, 20*b*, 20*c*), the time-series expression 30 (30*a*, 30*b*), and the error vector expression 31 (31*a*). In this embodiment, while therapy is implemented, as the measured irradiation position relative data, the position data that has passed through the position monitors 12*a* and 12*b* is utilized; in the case of calibration conducted first thing in the morning of a day or maintenance work, as the measured irradiation position relative data, the magnetic-field data on the charged particle beam 1 detected by the magnetic-field sensors 8 and 9 can be utilized. Because a great number of expressions for readily grasping the irradiation position accuracy can be dealt with, the convenience increases, whereby data collection conforming to the situation can be performed and hence determination on the irradiation position accuracy can be made.

Embodiment 4

Figure 14:
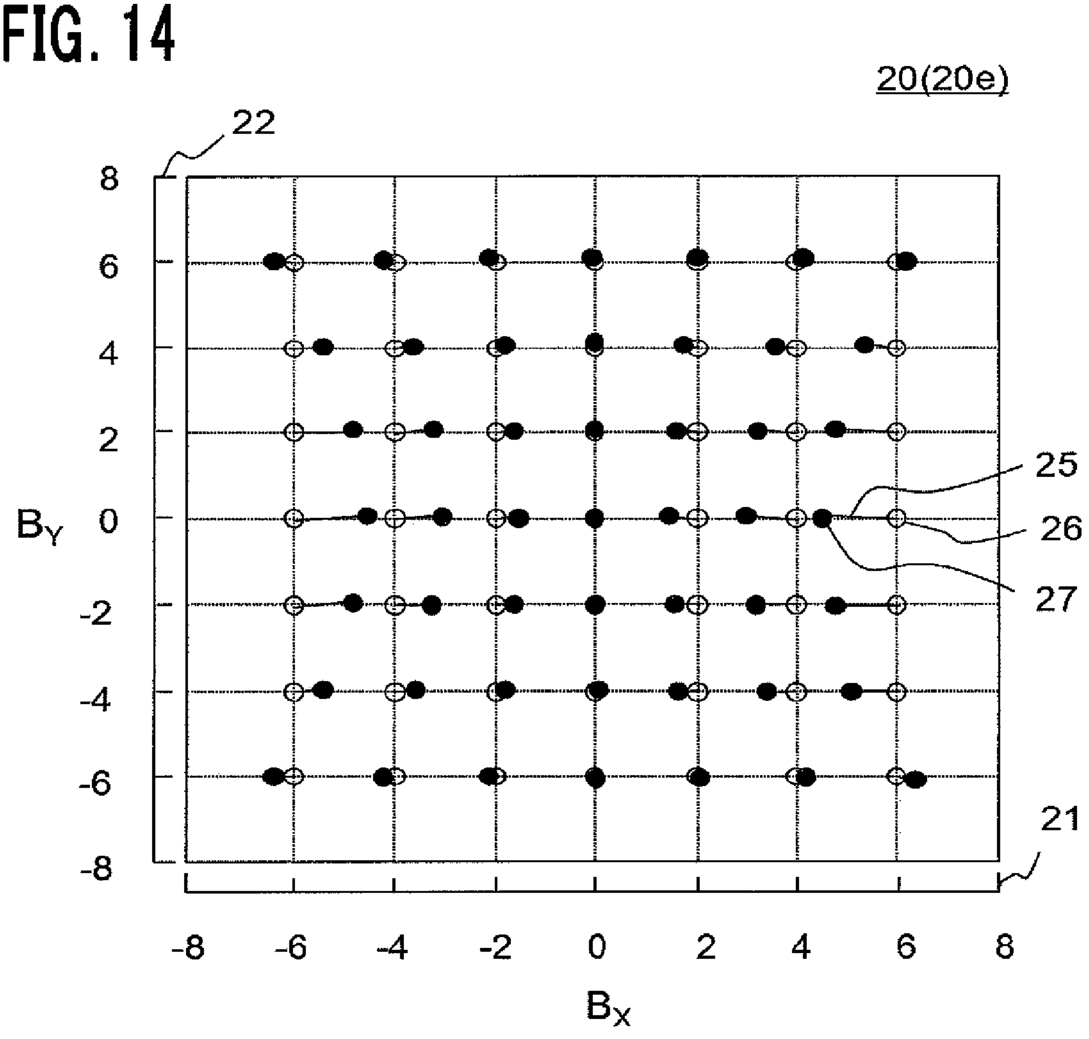
FIG. 14 is a chart representing first pincushion expression according to Embodiment 4 of the present invention.
Figure 15:
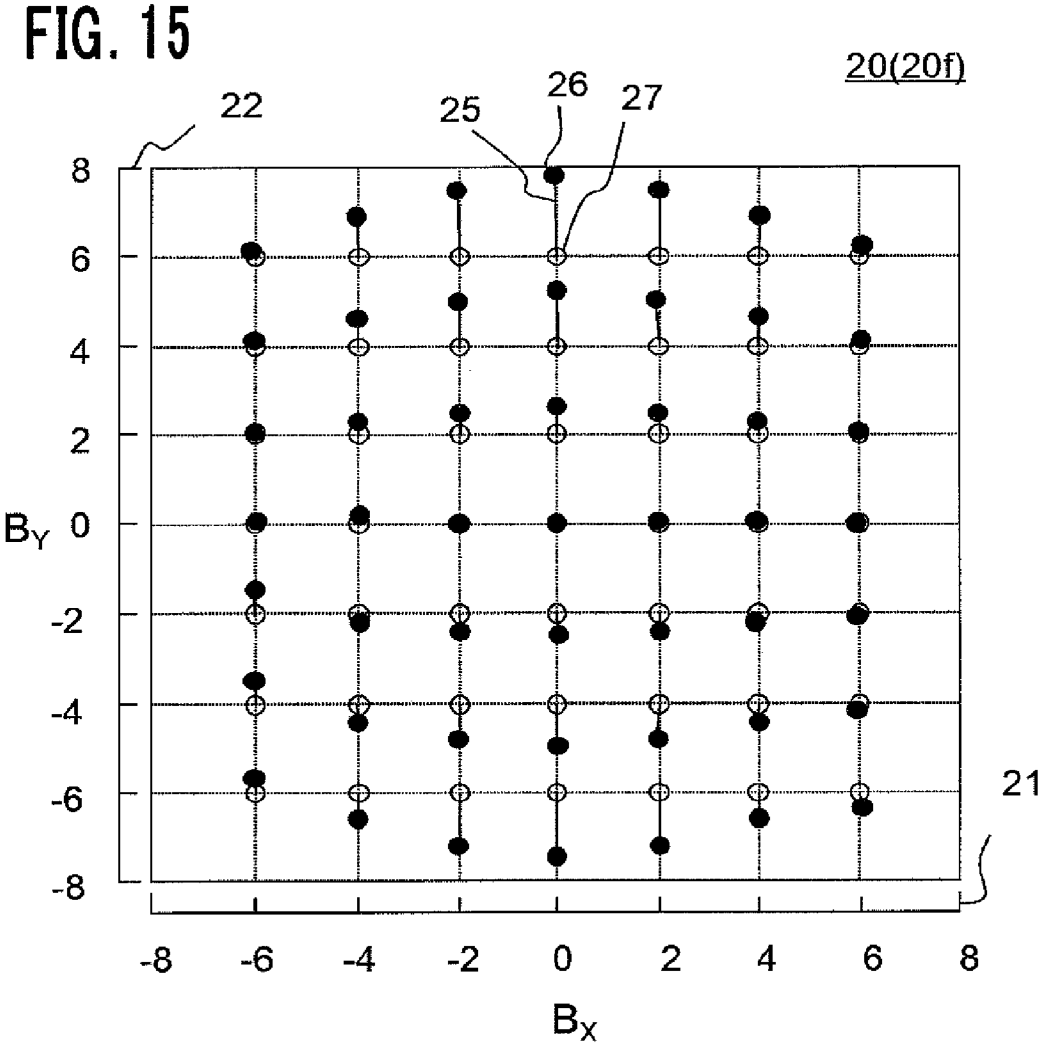
FIG. 15 is a chart representing second pincushion expression according to Embodiment 4 of the present invention.

In Embodiment 3, there has been described an example of pincushion expression in which the irradiation-region relevant region is represented by a magnetic-field space. In Embodiment 4, there will be described a method in which respective deformation coefficients for the X-direction component and the Y-direction component are provided. FIG. 14 is a chart representing first pincushion expression according to Embodiment 4 of the present invention; FIG. 15 is a chart representing second pincushion expression according to Embodiment 4 of the present invention. FIG. 14 is an example representing pincushion expression 20 (20*e*) in the case where the X-direction deformation is of magnification "30" and the Y-direction deformation is of magnification "1". FIG. 15 is an example representing pincushion expression 20 (20*f*) in the case where the X-direction deformation is of magnification "1" and the Y-direction deformation is of magnification "30".

In the case where the respective deformation coefficients for X direction and Y direction are provided, the magnetic-field error $B_{error}$ can be given by the equation (11), and the measured magnetic field $B_{def}$ obtained by deforming the magnetic-field error can be given by the equation (12). As explained in Embodiment 3, the desired magnetic field $B_{desired}$, the measured magnetic field $B_{measured}$, the measured magnetic field $B_{def}$ obtained by deforming the magnetic-field error, and the magnetic-field error $B_{error}$ are all expressed by vectors.

$$B_{desired} = \begin{bmatrix} b_{desired\_x} \\ b_{desired\_y} \end{bmatrix} \quad (9)$$

$$B_{measure} = \begin{bmatrix} b_{\_x} \\ b_{\_y} \end{bmatrix} \quad (10)$$

$$\begin{aligned} B_{error} &= B_{measured} - B_{desired} \\ &= \begin{bmatrix} b_{desired\_x} \\ b_{desired\_y} \end{bmatrix} - \begin{bmatrix} b_{\_x} \\ b_{\_y} \end{bmatrix} =: \begin{bmatrix} b_{error\_x} \\ b_{error\_y} \end{bmatrix} \end{aligned} \quad (11)$$

$$\begin{aligned} B_{def} &= B_{desired} + K(B_{error}) \\ &= \begin{bmatrix} b_{desired\_x} \\ b_{desired\_y} \end{bmatrix} + \begin{bmatrix} k_{\_x} & 0 \\ 0 & k_{\_y} \end{bmatrix} \begin{bmatrix} b_{error\_x} \\ b_{error\_y} \end{bmatrix} \\ &=: \begin{bmatrix} b_{def\_x} \\ b_{def\_y} \end{bmatrix} \end{aligned} \quad (12)$$

where "K" denotes a deformation coefficient matrix, and $k_{\_x}$ and $k_{\_y}$ denote an X-direction deformation coefficient and a Y-direction deformation coefficient, respectively.

The effect of the method in which the respective deformation coefficients for X direction and Y direction are provided is demonstrated in that because the scanning electromagnets 10 and 11 for scanning the charged particle beam 1 are separated from each other for the X direction and the Y direction, the tendencies of the X-direction and the Y-direction magnetic-field error $B_{error}$ can be viewed separately.

Because as is the case with Embodiment 3, the particle beam irradiation apparatus 61 according to Embodiment 4 is provided with the data processing apparatus 28 having the four functions, the irradiation position accuracy of the charged particle beam 1 can be displayed in such a way that the magnetic field ($B_X$, $B_Y$), which is the irradiation position relevant value PR related to the irradiation position P, and the magnetic-field error $B_{error}$, which is the irradiation position relevant value error $PR_{error}$, correspond to each other. Therefore, the user can intuitively and easily understand the foregoing display, and can readily grasp the irradiation position accuracy displayed in such a way that the irradiation position relevant value PR related to the irradiation position P of the charged particle beam 1 and the irradiation position relevant value error $PR_{error}$ correspond to each other. As a result, it is made possible to appropriately maintain the irradiation position accuracy and to perform the maintenance. In addition, the respective tendencies of the X-direction and the Y-direction positional error $B_{error}$ can separately be viewed; thus, there can readily be made consideration as to in which direction (the X direction or the Y direction) and how much correction is implemented.

Additionally, it may be allowed that on the display unit screen of the data processing apparatus 28, other expressions for supplementing the pincushion expression 20, i.e., as is the case with Embodiment 3, the X-direction error time-series expression 30 (30*c*), the Y-direction error time-series expression 30 (30*d*), and the error vector expression 31 (31*b*) are concurrently implemented.

Embodiment 5

Each of Embodiments 1 through 4 has been explained as the function of the data processing apparatus 19 or 28. However, as described in Embodiment 1, it may be allowed that as the data processing apparatus, dedicated hardware is utilized or ether a universal personal computer or a workstation is utilized. That is to say, the core of the present invention is a method of realizing the pincushion expression 20. The method of realizing the pincushion expression 20 can be achieved by implementing a program, which is software. Accordingly, in Embodiment 5, the program will be explained.

Figure 16:
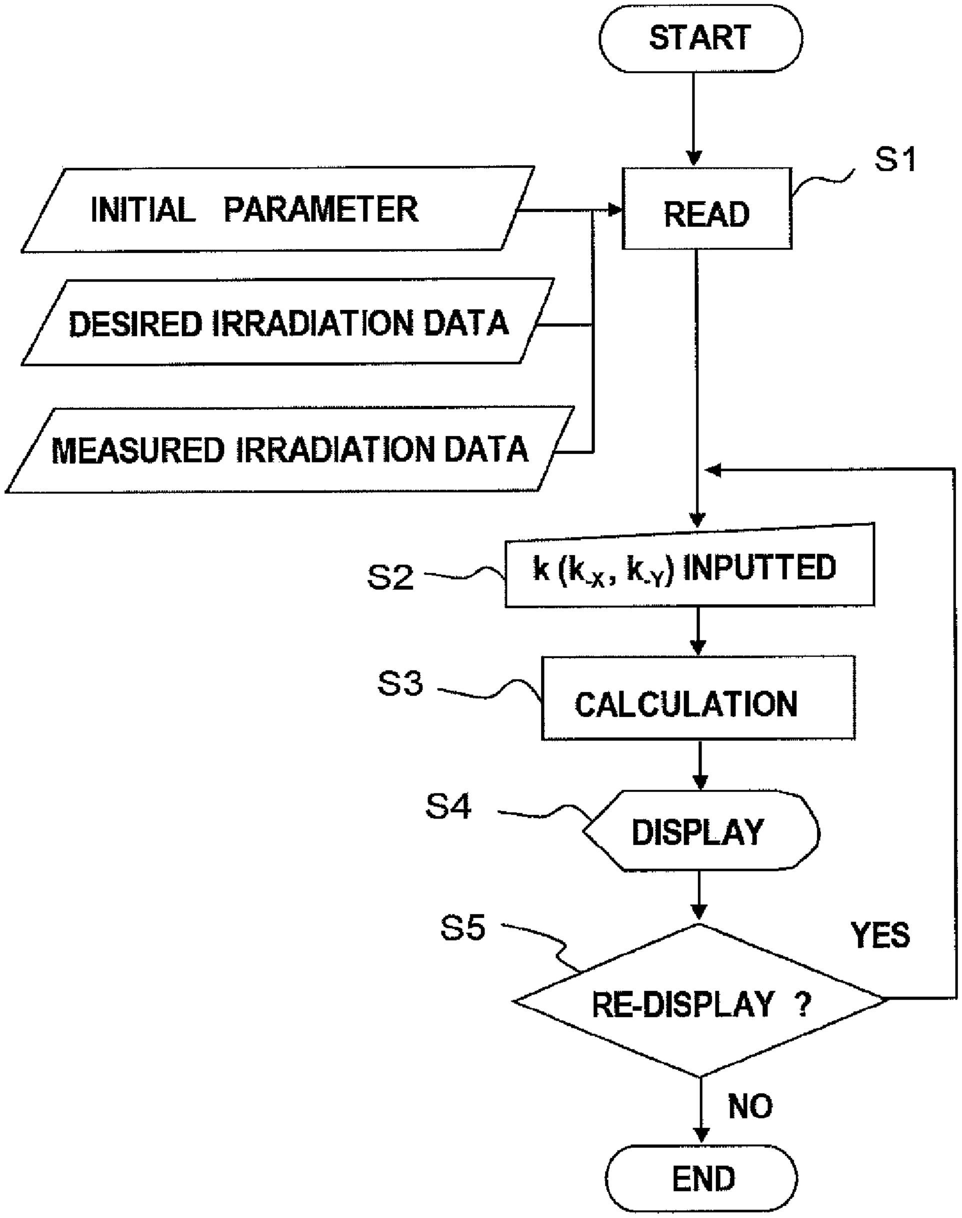
FIG. 16 is a flowchart for a data display program according to Embodiment 5 of the present invention.

FIG. 16 is a flowchart for a data display program according to Embodiment 5 of the present invention. With reference to FIG. 16, the flow of the present invention will be explained. At first, when the program is started, there is implemented a step (the step S1) in which various kinds of data pieces are read. The various kinds of data pieces to be read include initial parameters, desired irradiation data, and measured irradiation data. The desired irradiation data denotes data on the desired irradiation position relevant value related to a desired irradiation position or data on the desired irradiation position. The measured irradiation data denotes data on the measured irradiation position relevant value related to an irradiation position. Specifically, in each of the examples in embodiments 1 and 2, the measured irradiation data is data on a desired irradiation position relevant value or data on a desired irradiation position, and the measured irradiation data is data on a measured irradiation position relevant value. In each of the examples in Embodiments 3 and 4, the desired irradiation data and the measured irradiation data are data on a desired magnetic field and data on a measured magnetic field, respectively. The initial parameters herein are parameters indicating the range of an irradiation region (irradiation-region relevant region), the default value of a deformation coefficient, the color of a pincushion displayed on a screen, and the like.

Next, there is implemented a step (the step S2) in which the deformation coefficient k represented by the equation (2) or (8) and the deformation coefficients $k_{\_x}$ and $k_{\_y}$ represented by the equation (6) or (12) are inputted. In this situation, the operator who makes this program run inputs necessary deformation coefficients through a keyboard or the like.

The action of designating and inputting the deformation coefficient k represented by the equation (2) or (8) is substantially the same as the action of substituting a single and the same value "k" for the deformation coefficients $k_{\_x}$ and $k_{\_y}$ represented by the equation (6) or (12).

Next, there is implemented a step (the step S3) in which by use of the equation (6) or (12), the measured irradiation position $P_{def}$ obtained by deforming an error, the deformed measured irradiation position relevant value $PR_{def}$, and the measured magnetic field $B_{def}$ are calculated. Next, there is implemented a step (the step S4) in which by use of the first through fourth functions explained in Embodiments 1 and 3, the pincushion expression 20 is displayed on the display (display unit). The process from the step S1 through the step S4 is the flow of the basic function.

In this program, there are further provided a module for re-inputting the deformation coefficient and a module for performing re-display so that re-display can be performed, as may be necessary, by changing the deformation coefficient k ($k_{\_x}$, $k_{\_y}$). In the step S5, it is determined whether or not a command for implementing re-display processing; in the case where re-display is performed, the step S5 is followed by the step S2. In the case where re-display is not performed, the processing is ended. The operator who makes this program run calls for these modules, as may be necessary; specifically, for example, by clicking a designated button on the screen, the pincushion can be re-displayed.

As described above, in the data display program according to Embodiment 5, there are implemented the step of inputting the desired irradiation data, which is data on the desired irradiation position relevant value $PR_{desired}$ ($B_{desired}$) related to the desired irradiation position of the charged particle beam 1, and the measured irradiation data, which is data on the measured irradiation position relevant value $PR_{measured}$ ($B_{measured}$) related to the irradiation position of the charged particle beam 1; the step of inputting the deformation coefficient k; the step of calculating, in a display region which is the reproduction of the irradiation-region relevant region related to the irradiation region of the charged particle beam 1, the display coordinates $PR_{def}$ ($B_{def}$), which are coordinates obtained by adding the desired irradiation position relevant value $PR_{desired}$ ($B_{desired}$) to the coordinates obtained by arithmetically operating with the deformation coefficient k the irradiation position relevant value error $PR_{error}$ ($B_{error}$), which is the error in the measured irradiation position relevant value $PR_{measured}$ ($B_{measured}$) from the desired irradiation position relevant value $PR_{desired}$ ($B_{desired}$); and the step of displaying, in a display region which is the reproduction of the irradiation-region relevant region, the measured value display figure 24 (26) indicating the measured irradiation position relevant value $PR_{measured}$ ($B_{measured}$) and the desired value display figure 23 (27) indicating the desired irradiation position relevant value $PR_{desired}$ ($B_{desired}$) at the display coordinates $PR_{def}$ ($B_{def}$) and at the coordinates of the desired irradiation position relevant value $PR_{desired}$ ($B_{desired}$), respectively, and displaying the line 25 that connects the measured value display figure 24 (26) with the desired value display figure 23 (27). Therefore, by utilizing, as hardware, a universal personal computer or a workstation, the data processing apparatus described in each of Embodiments 1 through 4 can be realized. As a result, the irradiation position accuracy can be displayed in such a way that the irradiation position relevant value PR (B) related to the irradiation position and the irradiation position relevant value error $PR_{error}$ ($B_{error}$) correspond to each other. Therefore, the user can intuitively and easily understand the foregoing display, and can readily grasp the irradiation position accuracy displayed in such a way that the irradiation position relevant value PR (B) related to the irradiation position of the charged particle beam 1 and the irradiation position relevant value error $PR_{error}$ ($B_{error}$) correspond to each other; thus, it is made possible to appropriately maintain the irradiation position accuracy and to perform the maintenance.

Moreover, in the data display program according to Embodiment 5, there are implemented the step of inputting the desired irradiation data, which is data on the desired irradiation position $P_{desired}$ of the charged particle beam 1, and the measured irradiation data, which is data on the measured irradiation position relevant value $PR_{measured}$ ($B_{measured}$) related to the irradiation position of the charged particle beam 1; the step of inputting the deformation coefficient k; the step of calculating, in a display region which is the reproduction of the irradiation region of the charged particle beam 1, the measured irradiation position $P_{measured}$ of the charged particle beam 1, based on the measured irradiation position relevant value $PR_{measured}$ ($B_{measured}$), and calculating the display coordinates $P_{def}$, which are coordinates obtained by adding the desired irradiation position $P_{desired}$ to the coordinates obtained by arithmetically operating with the deformation coefficient k the irradiation position error $P_{error}$, which is the error in the measured irradiation position $P_{measured}$ from the desired irradiation position $P_{desired}$; and the step of displaying, in a display region which is the reproduction of the irradiation region, the measured value display figure 24 (26) indicating the measured irradiation position $P_{measured}$ and the desired value display figure 23 (27) indicating the desired irradiation position $P_{desired}$ at the display coordinates $P_{def}$ and at the coordinates of the desired irradiation position $P_{desired}$, respectively, and displaying the line 25 that connects the measured value display figure 24 (26) with the desired value display figure 23 (27). Therefore, by utilizing, as hardware, a universal personal computer or a workstation, the data processing apparatus described in each of Embodiments 1 through 4 can be realized. As a result, the irradiation position accuracy can be displayed in such a way that the irradiation position P and the irradiation position error $P_{error}$ correspond to each other. Accordingly, the user can intuitively and easily understand the foregoing display, and can readily grasp the irradiation position accuracy displayed in such a way that the irradiation position P of the charged particle beam 1 and the irradiation position error $P_{error}$ correspond to each other. Therefore, it is made possible to appropriately maintain the irradiation position accuracy and to perform the maintenance.

Embodiment 6

Each of Embodiments 1 through 4 has been explained as a particle beam irradiation apparatus. Additionally, Embodiment 5 has been explained as a data display program. In Embodiment 6, there will be explained a mode in which a particle beam irradiation apparatus is integrated in a particle beam therapy system.

Figure 17:
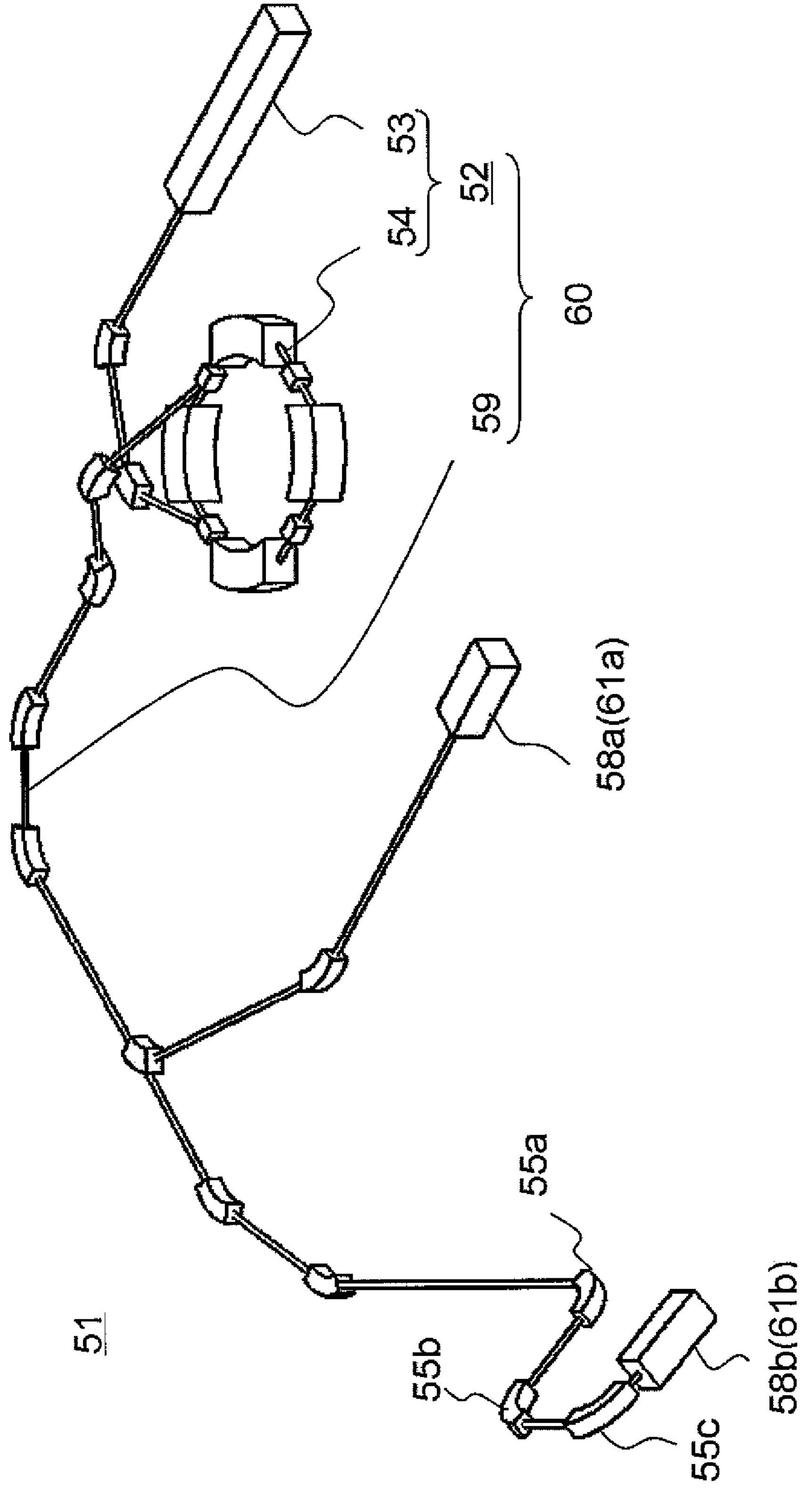
FIG. 17 is a configuration diagram illustrating a particle beam therapy system according to Embodiment 6 of the present invention.

FIG. 17 is a configuration diagram illustrating a particle beam therapy system according to Embodiment 6 of the present invention. A particle beam therapy system 51 includes a beam generation apparatus 52, a beam transport system 59, and particle beam irradiation apparatuses 58*a* and 58*b* (or 61*a* and 61*b*). The beam generation apparatus 52 includes an ion source (unillustrated), a prestage accelerator 53, and a synchrotron 54. The particle beam irradiation apparatus 58*b* (61*b*) is provided in a rotating gantry (unillustrated). The particle beam irradiation apparatus 58*a* (61*a*) is provided in a treatment room where no rotating gantry is installed. The function of the beam transport system 59 is to achieve communication between the synchrotron 54 and the particle beam irradiation apparatuses 58*a* and 58*b* (61*a* and 61*b*). A portion of the beam transport system 59 is provided in the rotating gantry (unillustrated), and in that portion, there are included a plurality of deflection electromagnets 55*a*, 55*b*, and 55*c*.

A charged particle beam 1, which is a particle beam such as a proton beam generated in ion source or a carbon beam (heavy particle beam) is accelerated by the prestage accelerator 53 and enters the synchrotron 54. The particle beam 1 is accelerated to have predetermined energy. The charged particle beam 1 is accelerated in a high-frequency electric field by the synchrotron 54 up to 70% to 80% of the light velocity, as it is being bent by means of the magnets. The charged particle beam 1 launched from the synchrotron 54 is transported to the particle beam irradiation apparatuses 58*a* (61*a*) and 58*b* (61*b*) by way of the beam transport system 59. In the beam transport system 59, the charged particle beam 1 that has received sufficient energy is guided through a path created with a vacuum duct to the particle beam irradiation apparatuses 58*a* (61*a*) and 58*b* (61*b*) in respective designated treatment rooms, while its orbit is changed by the electromagnets, as may be necessary. The particle beam irradiation apparatuses 58*a* (61*a*) and 58*b* (61*b*) each form an irradiation field in accordance to the size and the depth of the diseased site of a patient as an irradiation subject 18, and irradiate the charged particle beam 1 onto the irradiation subject 18 (refer to FIG. 1 or 9).

Meanwhile, in the foregoing sentence, the phrase "respective designated treatment rooms" has been describes; in general, in view of the therapy efficiency, a particle beam therapy system has a plurality of treatment rooms. That is to say, it is required to provide particle beam irradiation apparatuses 58 (61) as many as the number of treatment rooms. In many cases, a large-size complex system configured with a plurality of subsystems, in general, includes a sub-controller that is dedicated to control of each subsystem and a main controller that conducts and controls the whole system. The particle beam therapy system 51 according to Embodiment 6 of the present invention will be explained based also on a case where this configuration with a main controller and a sub-controller is adopted. For the sake of simplicity, the system including all subsystems in the beam generation apparatus 52 and the beam transport system 59 will be referred to as an accelerator system 60, herein. The system consisting of the particle beam irradiation apparatus 58 (61) and the rotating gantry will be referred to as an "irradiation system". FIG. 17 illustrates a case where there exist two treatment rooms, i.e., a horizontal irradiation room and a gantry irradiation room. Meanwhile, in general, as the controller of the particle beam therapy system 51, a workstation or a computer is utilized. Accordingly, in many cases, the controller is referred to as a "computer".

Figure 18:
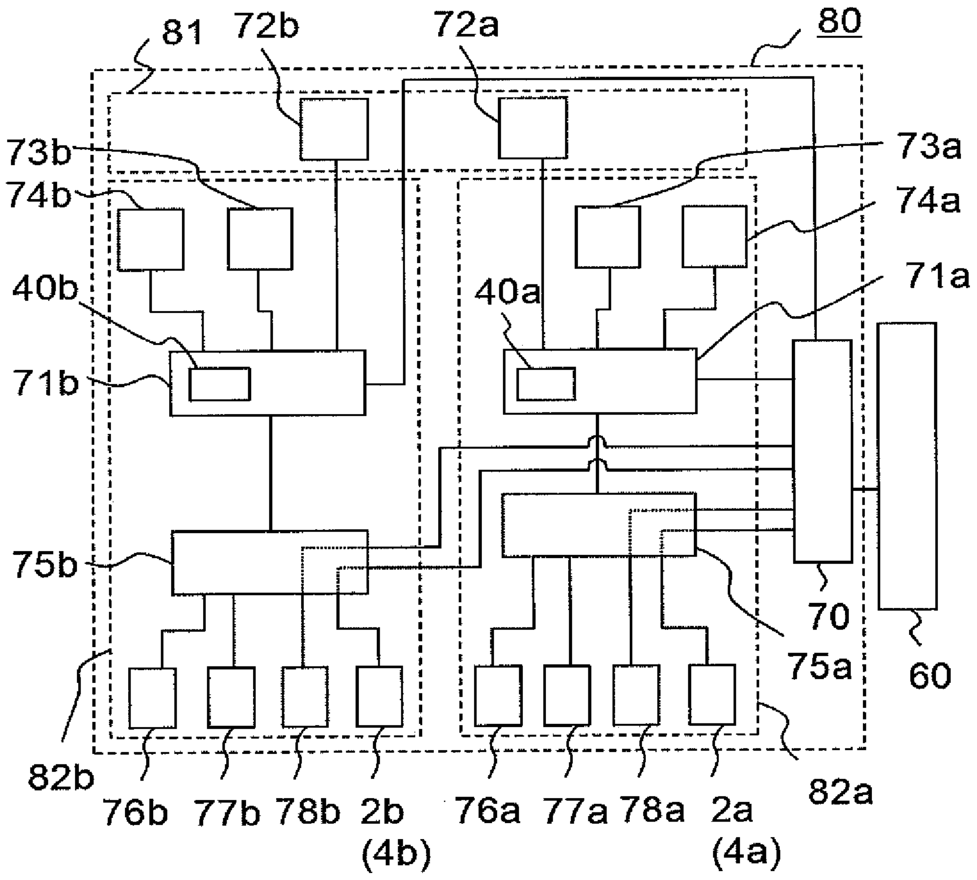
FIG. 18 is a control block diagram illustrating a particle beam therapy system according to Embodiment 6 of the present invention.

FIG. 18 is a control block diagram illustrating a particle beam therapy system according to Embodiment 6 of the present invention. With reference to FIG. 18, it will be explained what kind of system controls the particle beam therapy system 51. A main controller 70 corresponds to an irradiation system common computer. Sub-controllers 71*a* and 71*b* correspond to apparatus control computers. As described above, the particle beam therapy system 51 includes the main controller 70, the sub-controller 71*a*, and the sub-controller 71*b*. An irradiation system 80 is configured with the main controller 70, apparatuses arranged in an irradiation operation room 81, and apparatuses arranged in treatment rooms 82*a* and 82*b*. In the treatment room 82*a*, there is arranged an irradiation apparatus unit 2*a* of the particle beam irradiation apparatus 58 or an irradiation apparatus unit 4*a* of the particle beam irradiation apparatus 61. In the treatment room 82*b*, there is arranged an irradiation apparatus unit 2*b* of the particle beam irradiation apparatus 58 or an irradiation apparatus unit 4*b* of the particle beam irradiation apparatus 61.

The "consoles" 72*a*, 72*b*, 73*a*, 73*b*, 74*a*, and 74*b* connected with the sub-controllers 71*a* and 71*b* are each a keyboard, a display, or the like or a terminal such as a controller box; in other words, they are each a man-machine interface. The consoles 72*a* and 72*b* are provided in the irradiation operation room 81; the consoles 73*a* and 74*a* are provided in the treatment room A (82*a*); the consoles 73*b* and 74*b* are provided in the treatment room B (82*b*). Control boards 75*a* and 75*b* are connected with the bottom parts of the sub-controllers 71*a* and 71*b*, respectively. Each of the control boards 75*a* and 75*b* includes, specifically, a driver, an amplifier, a sequencer, and the like for various kinds of apparatuses 76*a*, 76*b*, 77*a*, and 77*b*, which are control subjects. The control board 75*a* lets signals between the main controller 70 and a respiratory navigation apparatus 78*a* and between the main controller 70 and the irradiation apparatus unit 2*a* (4*a*) pass; the control board 75*b* lets signals between the main controller 70 and a respiratory navigation apparatus 78*b* and between the main controller 70 and the irradiation apparatus unit 2*b* (4*b*) pass. The apparatuses 76*a* and 77*a*, the respiratory navigation apparatus 78*a*, and the irradiation apparatus unit 2*a* (4*a*) are connected with the bottom part of the sub-controllers 71*a* by way of the control board 75*a*; the apparatuses 76*b* and 77*b*, the respiratory navigation apparatus 78*b*, and the irradiation apparatus unit 2*b* (4*b*) are connected with the bottom part of the sub-controllers 71*b* by way of the control board 75*b*. Each of the apparatuses 76*a*, 76*b*, 77*a*, and 77*b* is, specifically, a motor for moving the respective axles of a treatment table, a motor for driving an X-ray image-capturing device in the irradiation apparatus, or the like.

The motor for the treatment table and the motor for the X-ray image-capturing device are not moved when a beam is being irradiated. That is to say, it is not required to implement control in synchronization with the electromagnet for the accelerator and the like controlled by the accelerator system 60. In order to exchange information about their conditions, the main controller 70 and the sub-controller 71*a* or 71*b* communicate with each other, for example, by use of a Ready signal that indicates in which treatment room the irradiation apparatus unit 2*a* (4*a*), 2*b* (4*b*) has completed its positioning and is ready to irradiate a beam, and a signal that indicates in which treatment room the irradiation apparatus unit 2*a* (4*a*), 2*b* (4*b*) has irradiated a beam and completed its irradiation. Briefly speaking, it is regarded as carrying out events sequentially.

The functions of the main controller 70 include management of irradiation such as "the irradiation apparatus units of which treatment rooms compete for the accelerator". However, in the case where higher-grade irradiation needs to be implemented, there occur the circumstances where it is required to control other apparatuses in synchronization with the accelerator system 60. For example, respiration-synchronized irradiation or respiratory-navigation irradiation corresponds to this case. In the case where there exist apparatuses (respiratory navigation apparatuses 78*a* and 78*b*) to be controlled in synchronization with the accelerator system 60, the configuration becomes as illustrated in FIG. 18.

In FIG. 18, commands to the respiratory navigation apparatus 78*a* and 78*b* are transmitted not from the sub-controllers 71*a* and 71*b*, respectively, but directly from the main controller 70. This is because by further decreasing the number of the apparatuses to be passed through, the problem posed by wasteful time (delay) is prevented, although it is conceivable to operate the main controller 70 in synchronization with the sub-controllers 71*a* and 71*b*. Because the irradiation apparatus units 2*a* (4*a*) and 2*b* (4*b*) need to be controlled in such a way as to be synchronized with the accelerator system 60, the irradiation apparatus units 2*a* (4*a*) and 2*b* (4*b*) are controlled by the main controller 70 for the same reason. The other function of the main controller 70 is to command the whole particle beam therapy system, as described above; thus, the functions thereof include control of apparatuses that need to be controlled in synchronization with the accelerator system 60.

In consideration of the above facts, it has been described that in general, as each of the main controller 70 and the sub-controllers 71*a* and 71*b* of the particle beam therapy system 51, a workstation or a computer is utilized. Additionally, in Embodiment 5, it has been explained that the data display program according to the present invention can be implemented by a universal workstation or computer. Accordingly, when the data display program described in Embodiment 5 is implemented on the main controller (irradiation system common computer) 70 or the sub-controllers (apparatus control computers) 71*a* and 71*b* of the particle beam therapy system 51, there is demonstrated an advantage that the hardware can commonly be utilized.

Furthermore, when the data display program is implemented on the main controller (irradiation system common computer) 70 or the sub-controllers (apparatus control computers) 71*a* and 71*b* of the particle beam therapy system, there is demonstrated an advantage that the pincushion expression 20 is performed in real time. FIG. 18 illustrates an example where the data display program is installed in the sub-controllers 71*a* and 71*b*. Data processing units 40*a* and 40*b* of the sub-controllers 71*a* and 71*b* implement processing according to the procedure of the data display program. When the pincushion expression 20 is performed in real time, the person who utilizes the particle beam therapy system 51 can not only ascertain the progress of the irradiation but also display in real time the irradiation position accuracy of the charged particle beam 1 in such a way that the irradiation position P and the irradiation position error $P_{error}$ correspond to each other. Additionally, the irradiation position accuracy of the charged particle beam 1 can be ascertained in such a way that the irradiation position relevant value PR (magnetic field) related to the irradiation position P and the irradiation position relevant value error $PR_{error}$ (magnetic-field error) correspond to each other.

As described above, in the particle beam therapy system 51 according to Embodiment 6, there are provided the beam generation apparatus 52 that generates the charged particle beam 1 and accelerates it by means of the accelerator 54, the beam transport system 59 that transports the charged particle beam accelerated by the accelerator 54, and the particle beam irradiation apparatus 58 (61) that irradiates the charged particle beam 1 transported by the beam transport system 59 onto the irradiation subject 18; the particle beam irradiation apparatus 58 (61) is provided with the detectors 12*a* and 12*b* (8 and 9) that detect the measured irradiation position relevant value $PR_{measured}$ ($B_{measured}$) related to the irradiation position of the charged particle beam 1, and the data processing apparatus 19 (28) that displays on the display unit 43 the measured irradiation position relevant value $PR_{measured}$ ($B_{measured}$) and the irradiation position relevant value error $PR_{error}$ ($B_{error}$), which is the error of the measured irradiation position relevant value $PR_{measured}$ ($B_{measured}$) with respect to the desired irradiation position relevant value $PR_{desired}$ ($B_{desired}$) related to the desired irradiation position of the charged particle beam 1; and the data processing apparatus 19 (28) has the input unit 41 to which the measured irradiation position relevant value $PR_{measured}$ ($B_{measured}$) and the desired irradiation position relevant value $PR_{desired}$ ($B_{desired}$) are inputted, and the calculation unit 42 (44) that displays the desired value display figure 23 (27) at the coordinates of the desired irradiation position relevant value $PR_{desired}$ ($B_{desired}$) and the measured value display figure 24 (26) at the display coordinates $PR_{def}$ ($B_{def}$), which are coordinates obtained by adding the desired irradiation position relevant value $PR_{desired}$ ($B_{desired}$) to the coordinates acquired by arithmetically operating the irradiation position relevant value error $PR_{error}$ ($B_{error}$) with the deformation coefficient k, when the desired value display figure 23 (27) indicating the desired irradiation position relevant value $PR_{desired}$ ($B_{desired}$) and the measured value display figure 24 (26) indicating the measured irradiation position relevant value $PR_{measured}$ ($B_{measured}$) are displayed in a display region which is the reproduction of the irradiation-region relevant region related to the irradiation region of the charged particle beam 1, and that displays the line 25 that connects the measured value display figure 24 (26) with the desired value display figure 23 (27). Therefore, the irradiation position accuracy of the charged particle beam 1 can be displayed in such a way that the irradiation position relevant value $PR_{measured}$ ($B_{measured}$) related to the irradiation position and the irradiation position relevant value error $PR_{error}$ ($B_{error}$) correspond to each other. Therefore, the user can intuitively and easily understand the foregoing display, and can readily grasp the irradiation position accuracy displayed in such a way that the irradiation position relevant value $PR_{measured}$ ($B_{measured}$) related to the irradiation position of the charged particle beam 1 and the irradiation position relevant value error $PR_{error}$ ($B_{error}$) correspond to each other; thus, it is made possible to appropriately maintain the irradiation position accuracy and to perform the maintenance.

Moreover, in the particle beam therapy system 51 according to Embodiment 6, there are provided the beam generation apparatus 52 that generates the charged particle beam 1 and accelerates it by means of the accelerator 54, the beam transport system 59 that transports the charged particle beam 1 accelerated by the accelerator 54, and the particle beam irradiation apparatus 58 (61) that irradiates the charged particle beam 1 transported by the beam transport system 59 onto the irradiation subject 18; the particle beam irradiation apparatus 58 (61) is provided with the detectors 12*a* and 12*b* that detect the measured irradiation position relevant value $PR_{measured}$ related to the irradiation position of the charged particle beam 1, and the data processing apparatus 19 that calculates the measured irradiation position $P_{measured}$ measured of the charged particle beam 1, based on the measured irradiation position relevant value $PR_{measured}$, and displays on the display unit 43 the measured irradiation position $P_{measured}$ and the irradiation position error $P_{error}$, which is the error of the measured irradiation position $P_{measured}$ with respect to the desired irradiation position of the charged particle beam 1, in such a way that the measured irradiation position $P_{measured}$ and the irradiation position error $P_{error}$ correspond to each other; and the data processing apparatus 19 has the input unit 41 to which the measured irradiation position relevant value $PR_{measured}$ and the desired irradiation position $P_{desired}$ are inputted, and the calculation unit 42 that displays the desired value display figure 23 at the coordinates of the desired irradiation position $P_{desired}$ and the measured value display figure 24 at the display coordinates $P_{def}$, which are coordinates obtained by adding the desired irradiation position $P_{desired}$ to the coordinates acquired by arithmetically operating the irradiation position error $P_{error}$ with the deformation coefficient k, when the desired value display figure 23 indicating the desired irradiation position $P_{desired}$ and the measured value display figure 24 indicating the measured irradiation position $P_{measured}$ are displayed in a display region which is the reproduction of the irradiation region of the charged particle beam 1, and that displays the line 25 that connects the measured value display figure 24 with the desired value display figure 23. Therefore, the irradiation position accuracy of the charged particle beam 1 can be displayed in such a way that the irradiation position P and the irradiation position error $P_{error}$ correspond to each other. Accordingly, the user can intuitively and easily understand the foregoing display, and can readily grasp the irradiation position accuracy displayed in such a way that the irradiation position P of the charged particle beam 1 and the irradiation position error $P_{error}$ correspond to each other; thus, it is made possible to appropriately maintain the irradiation position accuracy and to perform the maintenance.

In addition, the present invention has been explained with an example of particle beam irradiation apparatus utilizing a spot scanning irradiation method is utilized; however, the present invention can be applied also to a particle beam irradiation apparatus utilizing a raster-scanning irradiation method. In the case of a particle beam irradiation apparatus utilizing the raster-scanning method, position data or magnetic field data obtained every predetermined sampling time can be utilized as the measured irradiation position relative data. Moreover, there can be obtained data on the folding point of the charged particle beam, and by performing sampling at a time corresponding to a predetermined position, the measured irradiation position relative data can be obtained.

Additionally, the present invention has been explained with an example where in pincushion expression, time-series expression, and error vector expression, the ordinate and the abscissa are arranged outside the chart; the ordinate and the abscissa may be arranged at the middle side of the chart as well as outside the chart.

DESCRIPTION OF REFERENCE NUMERALS

1: charged particle beam
8: magnetic-field sensor
9: magnetic-field sensor
10: X-direction scanning electromagnet
11: Y-direction scanning electromagnet
12*a*, 12*b*: position monitor
18: irradiation subject
19: data processing apparatus
23: desired irradiation position figure (desired value display figure)
24: measured irradiation position figure (measured value display figure)
25: line
26: desired magnetic-field display figure (desired value display figure)
27: measured magnetic-field figure (measured value display figure)
28: data processing apparatus
30: time-series expression
31: error vector expression
41: input unit
42: calculation unit
43: display unit
44: calculation unit
51: particle beam therapy system
52: beam generation apparatus
54: synchrotron
58, 58*a*, 58*b*: particle beam irradiation apparatus
59: beam transport system
61, 61*a*, 61*b*: particle beam irradiation apparatus
k, $k_{\_x}$, $k_{\_y}$: deformation coefficient.
P: irradiation position
$P_{desired}$: desired irradiation position
$P_{measured}$: measured irradiation position
$P_{error}$: positional error
$P_{def}$: measured irradiation position obtained by deforming positional error
PR: irradiation position relevant value
$PR_{desired}$: desired irradiation position relevant value
$PR_{measured}$: measured irradiation position relevant value
$PR_{error}$: irradiation position relevant value error
$PR_{def}$: measured irradiation position relevant value obtained by deforming irradiation position relevant value error
$B_{desired}$: desired magnetic field
$B_{measured}$: measured magnetic field
$B_{error}$: magnetic-field error
$B_{def}$: measured magnetic field obtained by deforming magnetic-field error

The invention claimed is:

1. A particle beam irradiation apparatus that scans by means of a scanning electromagnet a charged particle beam accelerated by an accelerator and irradiates the charged particle beam onto an irradiation subject, the particle beam irradiation apparatus comprising:

a detector that detects a measured irradiation position relevant value related to an irradiation position of the charged particle beam, and a data processing apparatus that displays on a display unit the measured irradiation position relevant value and an irradiation position relevant value error, which is an error of the measured irradiation position relevant value with respect to a desired irradiation position relevant value related to a desired irradiation position of the charged particle beam, in such a way that the measured irradiation position relevant value and the irradiation position relevant value error correspond to each other, wherein the data processing apparatus comprises;

an input unit that receives the measured irradiation position relevant value and the desired irradiation position relevant value; and a calculation unit that displays a desired value display figure indicating the desired irradiation position relevant value at the coordinates of the desired irradiation position relevant value and a measured value display figure indicating the measured irradiation position relevant value at display coordinates, which are coordinates obtained by adding the desired irradiation position relevant value to the coordinates acquired by arithmetically operating the irradiation position relevant value error with deformation coefficients, when the desired value display figure and the measured value display figure are displayed in a display region which is the reproduction of an irradiation-region relevant region related to an irradiation region of the charged particle beam, and that displays a line that connects the measured value display figure with the desired value display figure.

2. The particle beam irradiation apparatus according to claim 1, wherein the calculation unit comprises;

a measured value calculation unit that calculates the display coordinates and displays the measured value display figure at the display coordinates;

a desired value calculation unit that displays the desired value display figure at the coordinates of the desired irradiation position relevant value; and a line display calculation unit that displays a line that connects the measured value display figure with the desired value display figure.

3. The particle beam irradiation apparatus according to claim 1, wherein the detector is a position monitor that detects a passing position of the charged particle beam; the measured irradiation position relevant value is a value that is outputted by the position monitor in accordance with a position at which the charged particle beam passes through the position monitor; the desired irradiation position relevant value is a value of a type that is outputted by the position monitor in accordance with a position at which the charged particle beam should pass through the position monitor so as to realize irradiation at a desired irradiation position; the irradiation position relevant value error is a positional error that is the difference between the irradiation position and the desired irradiation position; and the irradiation-region relevant region is a region, on the position monitor, through which the charged particle beam can pass.

4. The particle beam irradiation apparatus according claim 1, wherein the detector is a magnetic-field sensor that detects a magnetic field of the scanning electromagnet; the measured irradiation position relevant value is a measured magnetic field that is a magnetic field detected by the magnetic-field sensor; the desired irradiation position relevant value is a desired magnetic field of the scanning electromagnet; the irradiation position relevant value error is a magnetic-field error that is the difference between the measured magnetic field and the desired magnetic field; and the irradiation-region relevant region is a magnetic-field region of the scanning electromagnet.

5. A particle beam irradiation apparatus that scans by means of a scanning electromagnet a charged particle beam accelerated by an accelerator and irradiates the charged particle beam onto an irradiation subject, the particle beam irradiation apparatus comprising:

a detector that detects a measured irradiation position relevant value related to an irradiation position of the charged particle beam; and a data processing apparatus that calculates a measured irradiation position of the charged particle beam, based on the measured irradiation position relevant value, and displays on a display unit the measured irradiation position and an irradiation position error, which is the error of the measured irradiation position with respect to a desired irradiation position of the charged particle beam, in such a way that the measured irradiation position and the irradiation position error correspond to each other, wherein the data processing apparatus comprises;

an input unit that receives the measured irradiation position relevant value and the desired irradiation position; and a calculation unit that displays a desired value display figure indicating the desired irradiation position at the coordinates of the desired irradiation position and a measured value display figure indicating the measured irradiation position at display coordinates, which are coordinates obtained by adding the desired irradiation position to the coordinates acquired by arithmetically operating the irradiation position error with deformation coefficients, when the desired value display figure and the measured value display figure are displayed in a display region which is the reproduction of an irradiation region of the charged particle beam, and that displays a line that connects the measured value display figure with the desired value display figure.

6. The particle beam irradiation apparatus according to claim 5, wherein the calculation unit comprises;

a measured value calculation unit that calculates the display coordinates and displays the measured value display figure at the display coordinates;

a desired value calculation unit that displays the desired value display figure at the coordinates of the desired irradiation position; and a line display calculation unit that displays a line that connects the measured value display figure with the desired value display figure.

7. The particle beam irradiation apparatus according to claim 5, wherein the detector is a position monitor that detects a passing position of the charged particle beam; and the measured irradiation position relevant value is a value that is outputted by the position monitor in accordance with a position at which the charged particle beam passes through the position monitor.

8. The particle beam irradiation apparatus according to claim 5, wherein the detector is a magnetic-field sensor that detects a magnetic field of the scanning electromagnet; and the measured irradiation position relevant value is a measured magnetic field that is a magnetic field detected by the magnetic-field sensor.

9. The particle beam irradiation apparatus according to claim 1, wherein the deformation coefficients include an X-direction deformation coefficient corresponding to the X direction of the irradiation region and a Y-direction deformation coefficient corresponding to the Y direction of the irradiation region; and the calculation unit calculates the display coordinates by use of the X-direction deformation coefficient and the Y-direction deformation coefficient.

10. The particle beam irradiation apparatus according to claim 1, wherein the deformation coefficient may be set to "1", a default value that is a value utilized last time, or an inputted value.

11. The particle beam irradiation apparatus according to claim 9, wherein each of the X-direction and the Y-direction deformation coefficient may be set to "1", a default value that is a value utilized last time, or an inputted value.

12. The particle beam irradiation apparatus according to claim 1, wherein the data processing apparatus displays on the display unit a time-series expression for displaying the irradiation position relevant value error in a time-series manner.

13. The particle beam irradiation apparatus according to claim 1, wherein the data processing apparatus displays on the display unit an error vector expression for displaying in a vector manner the irradiation position relevant value error, as the X-direction error corresponding to the X direction of the irradiation-region relevant region and the Y-direction error corresponding to the Y direction of the irradiation-region relevant region.

14. The particle beam irradiation apparatus according to claim 5, wherein the data processing apparatus displays on the display unit a time-series expression for displaying the irradiation position error in a time-series manner.

15. The particle beam irradiation apparatus according to claim 5, wherein the data processing apparatus displays on the display unit an error vector expression for displaying in a vector manner the irradiation position error, as the X-direction error corresponding to the X direction of the irradiation region and the Y-direction error corresponding to the Y direction of the irradiation region.

16. A particle beam therapy system comprising:

a beam generation apparatus that generates a charged particle beam and accelerates the charged particle beam by means of an accelerator;

a beam transport apparatus that transports a charged particle beam accelerated by the accelerator; and a particle beam irradiation apparatus that irradiates a charged particle beam transported by the beam transport system onto an irradiation subject, wherein the particle beam irradiation apparatus is the particle beam irradiation apparatus according to claim 1.

17. A computer-readable medium encoding a data display program that displays, on a display unit, data for a particle beam irradiation apparatus that scans by means of a scanning electromagnet a charged particle beam accelerated by an accelerator and irradiates the charged particle beam onto an irradiation subject, the data display program implementing:

the step of inputting desired irradiation data, which is data on a desired irradiation position relevant value related to a desired irradiation position of the charged particle beam, and measured irradiation data, which is data on a measured irradiation position relevant value related to an irradiation position of the charged particle beam;

the step of inputting deformation coefficients;

the step of calculating, in a display region which is the reproduction of the irradiation-region relevant region related to an irradiation region of the charged particle beam, display coordinates, which are coordinates obtained by adding the desired irradiation position relevant value to the coordinates obtained by arithmetically operating with the deformation coefficients an irradiation position relevant value error, which is the error of the measured irradiation position relevant value from the desired irradiation position relevant value; and the step of displaying, in a display region which is the reproduction of the irradiation-region relevant region, a measured value display figure indicating the measured irradiation position relevant value and a desired value display figure indicating the desired irradiation position relevant value at the display coordinates and at the coordinates of the desired irradiation position relevant value, respectively, and displaying a line that connects the measured value display figure with the desired value display figure.

18. A computer-readable medium encoding a data display program that displays, on a display unit, data for a particle beam irradiation apparatus that scans by means of a scanning electromagnet a charged particle beam accelerated by an accelerator and irradiates the charged particle beam onto an irradiation subject, the data display program implementing:

the step of inputting desired irradiation data, which is data on a desired irradiation position of the charged particle beam, and measured irradiation data, which is data on a measured irradiation position relevant value related to an irradiation position of the charged particle beam;

the step of inputting deformation coefficients;

the step of calculating, in a display region which is the reproduction of the irradiation region of the charged particle beam, a measured irradiation position of the charged particle beam, based on the measured irradiation position relevant value, and calculating display coordinates, which are coordinates obtained by adding a desired irradiation position to the coordinates obtained by arithmetically operating with the deformation coefficients an irradiation position error, which is the error of the measured irradiation position from the desired irradiation position of the charged particle beam; and the step of displaying, in a display region which is the reproduction of the irradiation region, a measured value display figure indicating the measured irradiation position and a desired value display figure indicating the desired irradiation position at the display coordinates and at the coordinates of the desired irradiation position, respectively, and displaying a line that connects the measured value display figure with the desired value display figure.

19. The particle beam irradiation apparatus according to claim 2, wherein the detector is a position monitor that detects a passing position of the charged particle beam; the measured irradiation position relevant value is a value that is outputted by the position monitor in accordance with a position at which the charged particle beam passes through the position monitor; the desired irradiation position relevant value is a value of a type that is outputted by the position monitor in accordance with a position at which the charged particle beam should pass through the position monitor so as to realize irradiation at a desired irradiation position; the irradiation position relevant value error is a positional error that is the difference between the irradiation position and the desired irradiation position; and the irradiation-region relevant region is a region, on the position monitor, through which the charged particle beam can pass.

20. The particle beam irradiation apparatus according to claim 2, wherein the detector is a magnetic-field sensor that detects a magnetic field of the scanning electromagnet; the measured irradiation position relevant value is a measured magnetic field that is a magnetic field detected by the magnetic-field sensor; the desired irradiation position relevant value is a desired magnetic field of the scanning electromagnet; the irradiation position relevant value error is a magnetic-field error that is the difference between the measured magnetic field and the desired magnetic field; and the irradiation-region relevant region is a magnetic-field region of the scanning electromagnet.

* * * * *